US012350089B2

(12) United States Patent
Flexman et al.

(10) Patent No.: US 12,350,089 B2
(45) Date of Patent: Jul. 8, 2025

(54) ADAPTIVE COLLIMATION FOR INTERVENTIONAL X-RAY

(71) Applicant: KONINKLIJKE PHILIPS N.V., Eindhoven (NL)

(72) Inventors: Molly Lara Flexman, Melrose, MA (US); Jochen Kruecker, Andover, MA (US); Ashish Sattyavrat Panse, Burlington, MA (US); Grzegorz Andrzej Toporek, Cambridge, MA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 140 days.

(21) Appl. No.: 18/273,052

(22) PCT Filed: Jan. 24, 2022

(86) PCT No.: PCT/EP2022/051436
§ 371 (c)(1),
(2) Date: Jul. 19, 2023

(87) PCT Pub. No.: WO2022/161898
PCT Pub. Date: Aug. 4, 2022

(65) Prior Publication Data
US 2024/0298995 A1 Sep. 12, 2024

Related U.S. Application Data

(60) Provisional application No. 63/142,167, filed on Jan. 27, 2021.

(51) Int. Cl.
*A61B 6/00* (2024.01)
*A61B 6/06* (2006.01)
*A61B 6/46* (2024.01)

(52) U.S. Cl.
CPC .............. *A61B 6/545* (2013.01); *A61B 6/06* (2013.01); *A61B 6/467* (2013.01)

(58) Field of Classification Search
CPC .. A61B 6/06; A61B 6/08; A61B 6/544; A61B 6/542; A61B 6/545; A61B 6/54;
(Continued)

(56) References Cited

U.S. PATENT DOCUMENTS

| 6,422,751 B1 | 7/2002 | Aufrichtig et al. |
| 7,340,033 B2 | 3/2008 | Mollus et al. |

(Continued)

FOREIGN PATENT DOCUMENTS

WO   WO-2018087083 A1 * 5/2018 ........... A61B 5/0064

OTHER PUBLICATIONS

Walters et al. Impact of collimation on radiation exposure during interventional electrophysiology., European Society of Cardiology, Europace (2012) 14, pp. 1670-1673.
(Continued)

*Primary Examiner* — Don K Wong

(57) ABSTRACT

A system (SYS) and related method for facilitating collimator adjustment in X-ray imaging or a radiation therapy delivery. The system comprises an input interface (IN) for receiving input data including i) an input image and/or ii) user input data including a partial collimator setting for a collimator (COL) of an X-ray imaging apparatus (IA). A collimator setting estimator (CSE) of the system computes a complemented collimator setting for the collimator based the input data. Preferably, the system uses machine learning.

14 Claims, 14 Drawing Sheets

(58) Field of Classification Search
CPC ... A61B 6/4064; A61B 5/1045; A61B 5/1031; A61B 5/103; A61B 5/1038; A61B 2005/1041; A61B 5/1069; A61B 5/1067; A61B 5/1077; A61B 5/1078
See application file for complete search history.

(56) References Cited

U.S. PATENT DOCUMENTS

| | | |
|---|---|---|
| 9,280,837 B2 | 3/2016 | Grass et al. |
| 10,624,602 B2 | 4/2020 | Chang et al. |
| 10,645,259 B2 | 5/2020 | Sharma et al. |
| 10,716,530 B2 | 7/2020 | Chang et al. |
| 11,074,478 B2 | 7/2021 | Mau et al. |
| 2015/0139389 A1 | 5/2015 | Eklund |
| 2015/0228071 A1 | 8/2015 | Jockel et al. |
| 2019/0030370 A1 | 1/2019 | Hibbard |
| 2020/0401916 A1 | 12/2020 | Rolfe et al. |

OTHER PUBLICATIONS

Selvaraju et al., "Grad-CAM: Visual Explanations from Deep Networks via Gradient-based Localization", Springer Science and Business Media, LLC, vol. 128, No. 2, 2019, arXiv:1610.02391, pp. 336-359.

Zeiler et al., "Adaptive Deconvolutional Networks for Mid and High Level Feature Learning", 2011 International Conference on Computer Vision, Barcelona, Spain, 2011 IEEE International Conference on Computer Vision, pp. 2018-2025.

International Search report and Written Opinion of PCT/EP2022/051436, dated Apr. 7, 2022.

\* cited by examiner

A)

B)

C)

D)

ADAPTIVE COLLIMATION FOR INTERVENTIONAL X-RAY

CROSS-REFERENCE TO PRIOR APPLICATIONS

This application is the U.S. National Phase application under 35 U.S.C. § 371 of International Application No. PCT/EP2022/051436, filed on Jan. 24, 2022, which claims the benefit of U.S. Provisional Patent Application Ser. No. 63/142,167, filed on Jan. 27, 2021. These applications are hereby incorporated by reference herein.

FIELD OF THE INVENTION

The invention relates to a system and method for facilitating collimator adjustment in X-ray imaging or in radiation therapy delivery, to a method of training a machine learning model for use in such as a system, to a computer program element, and to a computer readable medium.

BACKGROUND OF THE INVENTION

In certain medical interventions, such as percutaneous coronary intervention (PCI), a clinician sometimes needs to introduce into the patient one or more medical devices or tools, such as guide wires, catheters, etc.

The intervention may be performed under X-ray imaging guidance where one or more images are acquired by an imaging apparatus ("imager"), sometimes as a series to form a video feed, which is displayed real-time for the clinician (referred to herein as the "user") on a display device.

The displayed imagery allows the user to consider the lesion, organ, the introduced device/tool or, in general, a region of interest ("ROI"). For best diagnostic or therapeutic results, the ROI needs to be visualized in an appropriate pose which requires adapting an imaging geometry of the imager.

In the course of these, at times difficult and demanding interventions, the user may need to switch from one ROI to another in which case the imaging geometry of the imager may need to be readapted. For example, the user may start treating a stenosis in one branch of the coronaries, and then switch to another branch where a bifurcation has to be treated. Or the treatment protocol may require switching from one organ to a completely different organ in a completely different part of the human body. Imaging geometry adaptations, in particular when required multiple times, are cumbersome and time consuming. For example, exam table or C-arm motion takes time and adds to the overall procedure duration. Often, X-ray imaging continues during table motion to monitor for the current FOV and to allow the operator to determine if the desired imaging ROI has been reached, adding to the overall dose exposure to user and patient as incurred during the procedure.

Imaging geometry changes may include adaptation of the imager's collimator. The collimator is device that allows restricting the imager's X-ray beam in shape and/or size. The field of view ("FOV") of the imager may thus be focused on the ROI.

X-ray beam collimation is important for both patient dose and image quality. Studies have shown that the practice of routinely collimating to the minimum required visual field results in significant reduction in radiation exposure to patient and user. Changing the settings of the collimator is often cumbersome and time consuming.

Most x-ray systems require the user to collimate manually. Currently, collimation requires multiple user interaction steps to set up collimation. In some imaging systems there may be six or more different collimator components that need be positioned and angulated, for example, four shutters and two wedges. Each may require the user to interact with multiple physical actuators, or with multiple elements on a touch screen.

If the user takes the time to optimally adjust the collimator, then, once the imaged device, gantry, or patient table/couch is moved, the collimator may need to be re-adjusted. By very definition, the more aggressive or "tight" the user sets the initial collimation settings, the less likely they are to remain usable in another imaging geometry, because the likelihood that the region of interest is no longer in the FOV is higher. One example of this is during radial access where it is helpful to collimate to the device as it moves up the arm and into the body.

SUMMARY OF THE INVENTION

There may therefore be a need for an imaging support system to address at least one or more of the above mentioned shortcomings in current imaging systems.

The object of the present invention is solved by the subject matter of the independent claims where further embodiments are incorporated in the dependent claims. It should be noted that the following described aspect of the invention equally applies to the related methods, to the computer program element and to the computer readable medium.

According to a first aspect there is provided a system for facilitating collimator adjustment in X-ray imaging or in radiation therapy delivery, comprising;
    an input interface for receiving input data including user input data including a first collimator setting for a collimator of an X-ray imaging apparatus; and
    a collimator setting estimator configured to compute a second collimator setting for the collimator based the input data.

In embodiments, the input data further includes at least one input image acquired by the X-ray imaging apparatus. The input image may be a projection X-ray image at a current field of view of the imaging apparatus. The input image may be acquired at a lower dose than imagery acquired after the collimator setting is computed and applied. Preferably, fluoroscopic X-ray imaging is used with the proposed system. As single such input image may suffice, but a sequence of input images may be used instead, for a given projection direction. The sequence may include an initial un-collimated image, and then sequence of images as collimated at earlier time instants. The user input data may be specified in such an input image, such as collimator lines designated therein by user. The lines and the image may be processed together by the estimator to compute the second collimator setting. Providing the first collimator setting with the image makes the processing more robust.

The first collimator setting may be partial or incomplete, whilst the second collimator setting is completing or complementing the first, the partial, collimator setting. The first and second collimator settings together may hence form a complete collimator setting that can be used to control the collimator to achieve the user desired collimation.

In embodiments, the collimator setting estimator is implemented as a trained machine learning model. In some such embodiments, the second or completing collimator setting(s) are regressed at the final layer of the machine learning model.

Alternatively, the collimator setting estimator computes the second/complementing collimator setting based on output data provided by a trained machine learning model. In some such alternative embodiments, the said output data is not provided by the final layer, but as intermediate, internal, output by a hidden layer of the model. That is, in such embodiments, the output data produced by the machine learning model includes a feature map. Computing the feature map may involve using a non-linear activation function as opposed to output obtainable at a final output layer of the model where no such non-linear activation function is necessarily used, or where such an activation function is used differently.

In embodiments, the machine learning model is an artificial neural network.

Feature maps include activation maps for classification or regression tasks or derived feature maps, such as heat maps.

In general, information captured in feature maps represent weight activations (such as convolutional filters) of a given layer. Optionally, the feature map may be visualized. Feature maps may be represented in data structures similar to (input) imagery, but feature maps are different type of data than imagery. In imagery, contrast is conferred by intensity variations that represent how matter of the imaged object (patient, or parts thereof) interacted with the imaging signal, such as tissue-X-radiation interaction in X-ray imaging. Imagery is data in image domain, whilst a feature map is data in feature domain. Variations in a feature map represents how and which part of a machine learning model operates on features in the input image and/or on features at a higher level, abstracted from image domain. For example, the feature map represents what relevance is given (eg in terms of weights or other) by the machine learning model/algorithm to a given image feature in a given hierarchy. Feature maps have in general a higher dimension than the input imagery from which they are computed by the ML model/algorithm. Feature maps are data generated by a machine learning model. Specifically, feature map is in general multidimensional data generated by applying convolutional operations to an input. Feature map(s) may be suitable to extract or abstract features from image domain into higher dimensions in plural levels/hierarchies, abstracted from the image domain to define for example "features of features", or "features of features of features", and so on in higher hierarchies, depending on the depth of the machine learning model used. Feature maps may be dimensionally-reduced such as to 1D, 2D or 3D, and may be optionally color-coded to obtain derived features maps, also referred to herein as heat maps. Heatmap is thus a post-processed feature map. The post-processing to effect dimensional reduction of feature map may include weighted summation, such as gradient-based approaches, or simple flattening/resampling, such as a global pooling approach. Heatmaps may be used to represent globally how machine learning model operates/interprets the input data, either in training or deployment.

In embodiments, the model is an encoder-decoder model, such as an autoencoder. Autoencoder is a special case of an encoder-decoder, in which original input is reconstructed at is output i.e. input space is the same as output space. An encoder-decoder is more general and could decode the encoded data into any other desired output.

In embodiments, the collimator setting estimator includes a segmentor configured to segment the feature map or heat map into at least one segment, and wherein the computed complementing or second collimator setting is further based on said segment. Segmentors that cooperate with encoder-decoder type networks preferably operate on feature maps, whilst for autoencoder type networks, segmentor preferably operates on heatmaps. In autoencoder type networks, the feature map of any hidden layer may be used for segmentation. In a general encoder-decoder type network, preferably the feature map of the last layer is used. However, accessing feature map(s) from earlier layers are also envisaged. The segmentor may operate on color parameters in color space, such as hue, saturation, in case the feature map/heat map is color-coded.

The segmentor may itself be implemented as an ML model, or may be arranged as a conventional analytic processing path, such as SIFT or others.

Having the segmentor operating on feature or heat maps in feature space is more robust to unpredictable variations that may occur in real-word situations, as compared to operating on regressed imagery. If final output data were used instead of feature map, such segmentation will be most likely be very specific to a certain data type. But in feature space, the segmentations may be discovered automatically, in an unsupervised fashion, and are therefore more robust to variations in the data. Feature maps can hence be used more universally.

Computing end-to-end ML segmentation may require ground-truth data and is therefore very time consuming and costly. In the proposed embodiment, because segmentation happens in the feature space, the segmentation is simpler. The feature map may be color-coded and the segmentation can thus be based on color properties (such as hue, saturation, etc). Thus, whilst segmentation in image space is not excluded herein in some embodiments, segmentation in feature space is preferred herein.

Edges of in-feature map or in-heat-map based segmentation may be smooth because of operation of the non-linear activation functions that map into a range of values rather than into a binary set. The activation function output as represented by the feature map includes smooth transitions that can be interpreted as collimator settings and may provide information on collimator tightness.

The user input or additional input provided by the user may be based on the feature map or segmented feature map or heat map. Selection of values near or towards one end of the range of the activation function values may be interpreted as moderate collimation, whereas selection nearer the other end of the range may represent a more conservative, that is, more tighter collimator preference. In other words, the smooth activation function outputs provided by some machine learning models (deep learning) is harnessed herein for segmentation. The raw output of the activation function (without thresholding) is preferably used herein for segmentation.

In embodiments, the first/partial collimator setting includes a specification of a geometrical curve or line in an input image acquired by the imaging apparatus or in said activation map.

The user input may include one or more points, one or more parallel lines, oblique lines, or curves. This information is projected by the proposed system and method into collimator setting space. The user input, or an optional additional user input, may include indicating the said geometrical elements (point, lines, curves) in the feature map or the segmented feature map or heat map. The user input may be scalar and in the range of the activation function and may thus be taken as an indication of, and processed into, a collimator tightness setting.

In embodiments, the input data further includes an input image acquired by the X-ray imaging apparatus. Such an input image may represent the current field or view of the imaging apparatus. Processing such an input image is preferably envisaged herein in the feature map or heat map-based embodiments, where the machine learning model generates the feature map or heat map based on processing the input image. It is the feature maps or the heat maps that are then segmented, optionally based on the user input which specifies one or more elements in the segmented feature or heat map as the first or partial collimator setting. Based on the segmentation and based on this user input (or additional user input) the complemented or second collimator setting is computed.

In embodiments, the second collimator setting may be computed as isolines of the feature map or heatmap. A tightness of the collimation may be adjusted by adjusting threshold of the activation function.

The collimator setting is defined by one or more parameters, such as collimator lines(s). The second collimator setting is also envisaged herein as an improved, refined, more specific collimator setting than the first collimator setting. The first collimator setting may thus be thought of as a rough estimate, rather than being incomplete as is in envisaged in some embodiments mentioned above. In embodiments, the first and/or second collimator setting parameter specifies a collimation tightness.

In embodiments, the system comprises a user input device for capturing the user input data. The user input device may include any one or more of: a graphical user interface, an eye tracking device, a gesture detection device, and a voice processor.

In embodiments, the imaging apparatus is capable of assuming different imaging geometries, wherein the collimator setting estimator is to adjust the complemented collimator setting in response to the imaging apparatus changing its imaging geometry. This allows the user to quickly set even frequent and/or tight collimations during an imaging procedure/intervention. In embodiments, the second collimator setting parameter specifies a collimation tightness. In embodiments, the collimator setting estimator is to adjust a tightness of current complemented collimator setting based on receiving at the input interface an updated partial collimator setting. In another aspect there is provided a method of training the machine learning model of a system as per any one of the above embodiments.

In embodiments, the said method is unsupervised, but supervised schemes are not excluded herein.

In another aspect there is provided a method for facilitating collimator adjustment in X-ray imaging or radiation therapy delivery, comprising:
  receiving user input data including a first (such as a partial) collimator setting for a collimator of an X-ray imaging apparatus; and
  computing a second (eg, a complementing) collimator setting for the collimator based the user input data.

The complemented collimator setting complements the initial, partial collimator setting, together forming a complemented or complete collimator setting.

The proposed system allows for quickly setting a collimator. A complete parameter specification is not required, thus saving time and effort for the busy medical user. The system harnesses the provided user data and/or input image to estimate the user's preference and computes the complemented collimator setting parameters accordingly. The very same system can thus cater for individual use preferences for a number of users. The computed complemented collimator settings (parameter(s)) include the user provided ones (the first) and the additional (second) settings computed by the system that together preferably form an intended complete collimator setting. The complete collimator setting allows, preferably unambiguously, adjusting the collimator for use. The computed collimator settings may be used for operating the collimator in a symmetric or asymmetric manner.

In particular, a collimator tightness preference by the user may be derived by the system based at least on the provided first/partial collimator setting(s). The settings may be defined by collimator setting parameter(s)). The complemented collimator setting parameter(s) is/are computed to account for the said tightness preference.

The proposed ML-based setup is generic and not application-specific. There is no reliance on recognizing any particular features, anatomies/organs or devices in the patient's body. The system described herein can operate on any clinical application (organ, device, etc.) as the features that are used to set the collimation are not necessarily explicitly trained a priori. This is because it has been found that the user supplied input, such as one or more collimator lines, in particular in combination with the input image, already provide enough context for the ML system to properly predict the user intended collimation. Further, the "user-in-the-loop" aspect of the prosed system allows for improved specificity of collimation, while still significantly reducing the burden on the user.

Whilst the above described collimation facilitation is mainly envisaged herein for X-ray imaging, this is not at the exclusion of other applications such as radiation therapy delivery where collimations to contours of lesioned portions of tissue are called for. In this and other applications, collimation may be in 3D rather than in 2D as in X-ray projection imaging.

"Imaging geometry": in fluoroscopy or other X-ray or non-X-ray imaging modalities, this may include one or more (in any combination) or all of: angulation angle, rotation angle, translation etc. In general, Imaging geometry pertains to any setting or configuration that changes position or orientation of the optical axis, the imaginary axis that connects X-ray source and X-ray detector and/or setting/configuration of the imaging modality/apparatus that otherwise influences spatially the imaging FOV relative to the imaged subject, such as collimator settings. etc.

"User", as used herein, is someone who operates the imaging apparatus.

"patient object" may be human, animal or plant, microbiological (eg, in microscopic imaging), etc. but may also relate to inanimate "objects" such as in baggage screening, non-destructive material testing, etc.

In general, a "machine learning component" is a computerized arrangement that implements, or facilitates implementation, of a "machine learning" ("ML") algorithm. The machine learning model may be based on a ML "model". The ML component is configured to perform a task. In an ML algorithm, task performance improves measurably the (new) training data is used in the training, assuming the training data has a suitable distribution. The model is adapted based on the training data. The performance may be measured by objective tests when feeding the trained model with test data. The performance may be defined by requiring a certain error rate to be achieved for the given test data. See T. M Mitchell, *Machine Learning*, page 2, section 1.1, McGraw-Hill, 1997. The task of main interest herein is to implicitly or explicitly predict collimator setting parameters.

BRIEF DESCRIPTION OF THE DRAWINGS

Exemplary embodiments of the invention will now be described with reference to the following drawings, which are not to scale, wherein.

DETAILED DESCRIPTION OF EMBODIMENTS

Figure 1:
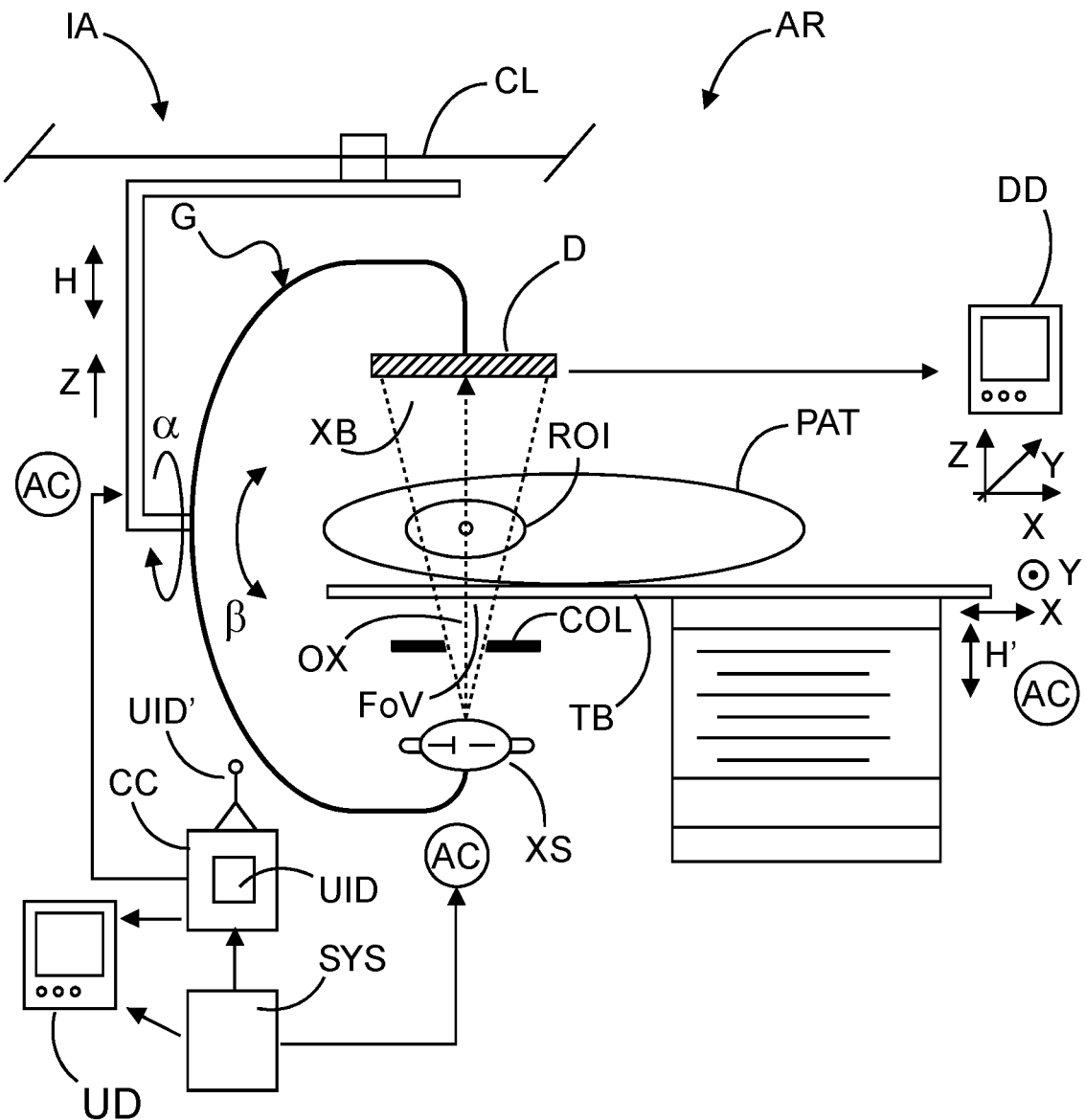
FIG. 1 is a schematic block diagram of an imaging arrangement.

With reference to FIG. 1 there is shown a schematic diagram of an arrangement AR for image-based support, preferably for use in the context of a medical intervention.

The arrangement AR comprises an imaging apparatus IA, in particular an x-ray imaging apparatus, operable by a user to obtain x-ray imagery $I_t$ of internal structures of a patient at a ROI. The ROI may be the human heart, the lungs or another organ or groups of organs.

The imagery $I_i$, sometimes referred to herein as a sequence of frames, may be displayed in real-time as a motion picture or video feed on a display device DD to the user, or may be displayed singly as a still image, as desired.

The imaging arrangement AR further comprises a user assistance system USYS configured to assist a user in adapting a collimator setting.

As mentioned, the imaging apparatus AI and the system USYS are mainly envisaged herein in embodiments to support medical interventions such as percutaneous coronary interventions (PCI). Other medical interventions, not necessarily performed in relation to the human or animal heart, are also envisaged, and so are non-medical applications. Such non-medical applications may include image-based support for examinations and works carried out in inaccessible caving or plumbing systems, or examination of technical equipment. Such technical equipment may include engines and other complex machinery that cannot be directly inspected by the unaided eye, but require imaging equipment to make occluded regions of interest accessible to visual inspection through a video feed or still image.

Referring now first in more detail to the imaging apparatus IA, this may be arranged as shown in the exemplary embodiment in FIG. 1 as an imaging apparatus of the C- or U-arm type. In the embodiment of FIG. 1, the C-arm system IA is ceiling CL mounted but this may not be necessarily so in all embodiments. Alternatively, the imaging apparatus IA is floor mounted, or mounted on a stand. etc. In further alternative, the imaging apparatus may be mobile, such as wheeled or track-mounted. A gantry G is not required herein such as in mobile X-ray devices where there is no or no permanent physical connection between detector D and tube XX.

The X-ray imaging apparatus includes an x-ray detector D and an x-ray source XS. Broadly, in embodiments, but not necessarily all embodiments, the imaging apparatus comprises the gantry G which carries the x-ray detector D and the x-ray source XS, such as an x-ray tube. The x-ray detector D and the x-ray source XS are arranged on the gantry G in opposed spatial relationship to form an examination region between the x-ray source and the x-ray detector. It is in this examination region that the patient PAT is situated so that the region of interest is positioned roughly at an iso-center of the IS imaging apparatus. The patient may lie on an examination table TB during the imaging. The table TB may be adjusted in height H, may be translatable along X, or Y, or both X and Y axis, and may also be tiltable in embodiments about a one or more tilt axis.

During the imaging procedure, the x-ray source XS is energized by applying a cathode current and a voltage across an anode and the cathode to produce an x-ray beam XB that issues forth from a focal spot of the anode. The beam exits the x-ray source, passes through the examination region, and hence through patient tissue at or around the region of interest, to then impinge on an x-ray sensitive surface of the x-ray detector D. The x-ray sensitive surface of detector D may comprise pixel elements that convert the impinging x-radiation into intensity values. The intensity values may vary from location to location, the variation being caused by differential attenuation of the x-ray beam due to different tissue types having locally different material densities.

The intensity values so recorded at the detector XS may be mapped into image values according to a color or grey value palette to form a projection image (or "frame"). Acquisition circuitry operates to capture in this manner at a suitable frame rate a sequence of different projection images at different instances during the imaging procedure. Exemplary frame rates envisaged herein are 20-30 fps. For instance, in fluoroscopy, as the main modality envisaged herein, intensity values may be mapped on a range of values ranging from black through grey values to white, with image values the darker the lower the intensity values. Other mapping schemes may be used, such as a reverse mapping, where lower intensity values are mapped to lighter image values, such as is commonly used in radiography. Still other mapping schemes may be used instead. Acquisition of a single or few still image such as in radiography is not excluded herein.

The spatial width of the (primary) x-ray beam defines the FoV of the imager IA. Objects that reside or extend into the field of view, and hence into the x-ray beam, will modify the intensity with which the x-ray is detected locally at the detector. The field of view may be changed by user request or automatically by adapting the imager IA's imaging geometry such as by moving the X-ray source, moving the patient, or by enlarging or restricting the beam width by using the collimator COL, or a combination of all or any subset of the foregoing components.

The X-ray detector may be arranged as a digital flat-panel detector communicatively coupled to the display device DD.

The flat-panel detector D may be of the direct conversion or indirect conversion type. In an alternative embodiment, the imaging detector may be arranged as an image intensifier coupled through a video camera to the display device.

Although the contrast conferring mechanism of the projection imagery mainly envisaged herein is attenuation, other imaging techniques that exploit, in addition or instead, other contrast mechanisms are not excluded herein such as phase contrast and/or dark-field imaging. In the latter two cases, the imaging apparatus may include additional components, such as an interferometer or other.

The imaging apparatus includes a control console CC through which the user can determine when to start and stop the imaging procedure, in particular when to energize the x-ray source XS. A pedal may be coupled to the console as a user interface to control energizing or de-energizing the x-ray source or to operate a grid switch to halt or resume exposure to the X-ray beam.

The main propagation direction of the primary x-ray beam (leaving aside scattered radiation) is defined by the optical axis OX which is an imaginary line that runs from the focal spot (not shown) of the x-ray source to a center portion of the x-radiation sensitive surface of the x-ray detector D. The optical axis defines the spatial projection direction.

In order to better support the user in navigation, a position or spatial orientation of the optical axis, and hence of the projection direction, may be changed on user request. This can be achieved in one embodiment by arranging the gantry to be rotatable around one, or preferably two, respective axes perpendicular to each other. Having two such rotational axes allows for 2 degrees of freedom for changing the optical axis. For instance, in one geometry one of the rotation axis extends into the drawing plane of FIG. 1 and allows the optical axis to be rotated around an angle $\beta$. The other rotation axis is parallel to the drawing plane of FIG. 1 and allows changing the orientation around another angle $\alpha$, independent of $\beta$, as schematically shown in FIG. 1. By convention, the axis for a defines "the rotation" whilst the axis for $\beta$ defines "the angulation".

Optionally, it is also the height of the gantry itself that may be changed as indicated by double arrow H in FIG. 1. In addition, the optical axis OX may be translated by moving the gantry accordingly along a line. Position and orientation of the optical axis may be referred to herein to at least partly define the imaging geometry. In other words, the imaging apparatus envisaged herein in embodiments allows the user to change the imaging geometry.

Changing the imaging geometry may be requested through the user by operating a joy-stick or other suitable user interface UID'. The user interface UID' may be coupled or integrated into to the control console CC.

The requesting of the change in imaging geometry may include causing control signals to be applied to suitable actuators AC arranged at the imaging apparatus such as at any one or more of the gantry, the table TB, collimator COL, etc. The actuators AC act in response to the control signals to change the imaging geometry. The actuators AC are either powered by a power source or are powered manually by the user through hand wheel, levers, etc or other devices. The actuators AC are either purely automatic or a hybrid, or semi-automatic. In the semi-automatic case, user operates user interfaces UID' such as a joystick or other control device, but may be assisted by a servo-motor or similar to effect the imaging geometry change.

The actuators are encoded or not. If they are encoded, they may include linear and or angular encoder such as potentiometers, or others. Thanks to the encoders, the image geometry change effected by one or more actuators is trackable, that is, is mappable to numerical coordinates that vary with the imaging geometry change.

Other options to change the imaging geometry may include changing the detector-x-ray source distance and/or changing the distance between the region of interest and the x-ray detector and hence the x-ray source. The latter change may be effected by changing the height H' of the examination table TB on which the patient lies. Changing height h and/or the source-detector distance may amount to a rescaling of the image at a certain magnification factor.

Yet another option to change the imaging geometry may include translating the patient table TB in a plane parallel to the surface of the table in X, Y direction, one direction being parallel to the drawing plane of FIG. 1 and the other extending into the image plane. The table may also be tiltable around one or more axes. Components of the imaging apparatus that take part in the imaging geometry change may be referred to herein generally as imaging geometry components and include in particular any one, more than one, or all of: the source XS, the gantry, the detector, the collimator COL, the table etc.

In general, a change in imaging geometry changes the spatial relationship between the x-ray source and/or detector relative to the region of interest. In addition or instead, the field of view may be changed by collimator action or by moving the patient for instance by table TB translation as described.

Turning now to the user assistance system USYS in more detail, this is configured to assist a user in adjusting a collimator setting of a collimator COL of the imaging apparatus IA.

Broadly, the user assistance system USYS for collimation adjustment co-operates with a user input device UID. The user device UID may include a graphical user interface (GUI). The GUI may be displayed on a user monitor UD. The user monitor UD may or may not be different from the display DD used to display the acquired imagery. Such a GUI based user input device UID may include one or more touch screen interfaces (TSN). The GUI may include one or more graphical components visualized on the user display device UD. The graphical components may include widgets, such as stylized buttons etc, with which the user can interact by touch screen action or by use of a pointer tool, to adjust the collimator. The pointer tool may be a computer mouse or a stylus or other. The user input device UID may support gesture recognition. More conventional user input by keyboard with textual or alphanumeric input captured in one or more text boxes is also envisaged.

Instead of, or in addition to, GUI-based embodiments, the user input device UID for collimator adjustment may (further) include a control panel with a set of one or more physical control elements, such as levers (eg, joystick), buttons, or other manually operable actuators. Such user interfaces with physical, manually operable, control elements are sometimes referred to as TSOs. In yet other embodiments the user interface device UID may further include, in addition or instead to the ones described above, other interface options, such as eye tracking devices, gesture tracking system. User interface devices with sound capturing and interpreting facilities are also envisaged to allow user voice command-based control. The user control device(s) UID may be integrated into augmented reality AR system in embodiments.

The collimator adjustment user device UID may be integrated at least in parts into an operator console unit CC. The unit CC is communicatively coupled by a wireless or wired communication channel to the actuator(s) AC of the imaging apparatus IA or to other hardware or software components of the said imaging apparatus IA.

Briefly, and as mentioned earlier, the user assistance system USYS as envisaged herein is capable of communicating with the collimator adjustment user interface device UID. Specifically, the user assistance system USYS receives a collimator setting request provided by the user through the user interface device UID. At least a part of the collimator setting is definable by one or more parameters, referred to herein as the collimator setting parameter(s) l. In the following, while we refer to collimator setting parameter(s) l in the plural, this is not to limit the present disclosure, as a setting definable by a single such parameter is not exclude herein and specifically envisaged herein in embodiments.

The user provided collimator setting parameters l are processed by the user assistance system USYS to compute complemented, that is, additional or improved collimator parameter setting(s). Yet more specifically, the user may only need to define the collimator setting parameters partially, with the user assistance system USYS computing a complete or, at least complemented, collimator setting parameters l'. The system USYS computes completing collimator setting parameters l*, so that l'=l∪l*. Computation of complementing collimator setting parameters l* is influenced by user provided (initial, likely incomplete) set of collimator setting parameters l The so completed collimator setting parameters l' allow to unambiguously define the collimator setting, or at least the degree of freedom for such a setting is reduced.

The complemented collimator setting l' may be displayed on the user display device UD or on any other display device (such as device DD), optionally concurrently with a current image acquired by the imaging apparatus IA. For example, the complemented collimator setting l' may be shown as an overlay graphic element, overlaid on the current image. In addition or instead, the complemented collimator setting parameters l' may be automatically translated by suitable middleware into control signals/commands, and forwarded via a communication channel to actuators AC of the imaging apparatus to instruct same to effect the requested collimator setting at collimator COL. Alternatively, the computed complemented collimator setting parameters l' may be displayed, with user interface option for the user to confirm the computed parameters. The control signal/command is then so forwarded only upon confirmation by the user, such as by touchscreen action or any other user input.

The user assistance system USYS thus allows a user to save time and efforts. Instead of the user having to specify with effort and time expenditure a complete set of collimator setting parameters, the system USYS assists the user in this task. The user needs only to provide a, possibly small, part of the collimator setting parameters l and the proposed system USYS predicts the remainder of the required collimator setting parameters l*. The user, experienced or not, may thus able to adjust the collimator setting more quickly. In some embodiments, a type of dynamic-loop control sub-system will readjust the remaining collimator setting parameters l* as soon as a new user defined collimator setting l is provided. The system may be considered closed-loop, with user being part of the loop ("in loop). The ability for quick collimator adjustments may be beneficial in real time interventions, in particular in contexts with high stress factor, such as trauma settings for instance, where frequent changes of imaging geometry (and thus the field of view) may be called for.

With reference to FIG. 2, the collimator system COL is described in more detail.

Figure 2A:
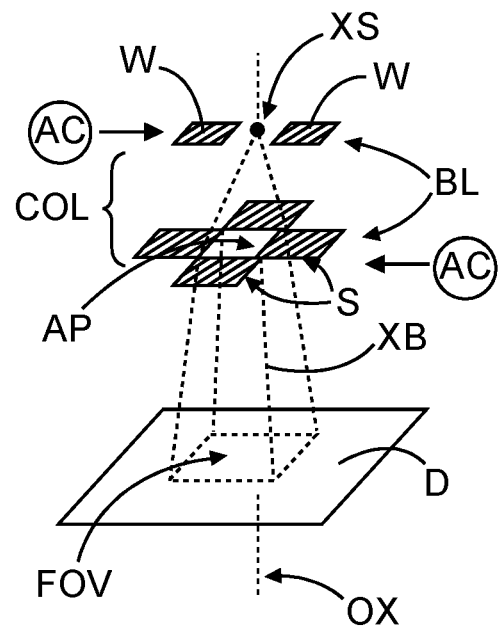
FIGS. 2A-2C show a perspective view of a collimator system of an x-ray imaging apparatus, and aspects of projection imagery obtainable by collimated x-ray exposures.

FIG. 2A) affords a perspective view of the collimator system COL, with other components of the imaging apparatus IA partly cut away to facilitate exposition. Broadly, the collimator system COL is configured to modify the x-ray beam XB emanating from the source XS. Specifically, the collimator system COL modifies this original beam in shape and/or size to define a width of the field of the view imaging apparatus. In other words, the collimator defines how much can be "seen" in the acquired image, given the current set of remaining imaging geometry settings, such a table and c-arm pose.

More specifically, the collimator system COL is operable to modify a cross section, in shape and size, of the x-ray beam in a plane perpendicular to a current pose of the optical axis OX. Such a beam modification may include restricting the cross section in order to allow saving x-radiation dose to patient and user, and to allow acquiring more focused imagery where only the region/anatomy of current interest (the ROI) is represented. The collimator COL allows adjusting the cross section of the x-ray beam by at least partially placing one or more of a plurality of radiation opaque collimator blades BL into the beam XB. The blades BL, made for example from lead, Tungsten or other high Z-material, will be referred to herein simply as "blades BL".

The blades BL are preferably motorized by one or more actuators AC to define the field of view FOV with desired shape and/or size. By motion of the blades, the FOV can be dynamically changed in shape and size as required by user and/or protocol. The blades BL may be rotatable along one or more axis. However, in some embodiments the motion of the blades as controlled by actuator AC is confined to a translation in a plane X,Y, perpendicular to the optical axis OX as shown in FIG. 2A). More than one set of such blades may be provided separated along the optical axis OX as is shown in FIG. 2A. One set of blades (four such blades are shown in FIG. 2A), but there can be more or less) may be referred to as shutters, whilst the other set, more proximal to the x-ray source XS along imaging axis OX, may be referred to herein as "wedges". In general, no distinction will be made herein between shutters and wedges, and both will be referred to herein simply as "blades BL", unless specifically named.

Figure 2B:
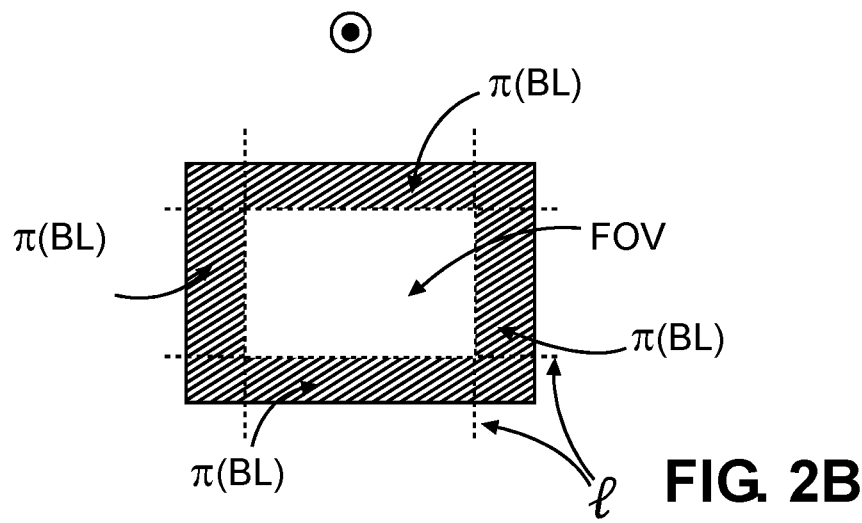

FIG. 2B) is a plan view along the optical axis OX (extending perpendicular into the drawing plane of FIG. 2B) of a collimated field of view FOV. The shadows or radiation footprints of the blades BL are indicated as Π(BL). In FIG. 2B), in consistency with FIG. 2A), four blades BL are shown, some or each movable towards the optical axis to restrict the field of view from one, more than one, or all sides. Thus, a smaller FOV size results, which can be enlarged again (up to the native cross-section of the beam XB at a given magnification), once some or all collimator blades are retracted, as desired by the user. Asymmetric collimation as opposed to symmetric collimation (shown in FIG. 2B)) is also envisaged herein, where only a sub-set of the collimator blades are actuated and moved into the beam XB. In asymmetric collimation some or each blade BL may be moved independently of one, some or all the other blade(s).

Projections of edges of the collimator blades proximal to the axis OX are represented in the projection image in FIG. 2B as a set of four lines, one line per collimator blade, which together define the field of view. These lines will be referred to herein as "collimator lines". Geometrically, each of these lines can be described by two parameters $ax+b$. A system of up to N such geometrical lines in the detector projection plane can be used as a geometrical device to define a desired collimator setting, with N being the number of blades. More specifically, the collimator lines themselves may represent one way of describing the collimator setting parameters. For this reason, in this disclosure we will using the "l"-notion to refer to both. However, other descriptions of the collimator setting parameters are also envisaged herein, such as in terms of control commands and/or blade position/rotation (in a length dimension and/or angles measured relative to a reference pose), user controller position (eg, joystick position) etc. The exact nature of the collimator settings parameters as specifiable/requestable by the user may depend on the type of user input device UID. However, no matter the nature of the collimator settings parameters, these can always be thought equivalent to a respective set of such collimator lines. We will thus refer herein to such collimator lines when referring to collimator setting parameters/collimator settings even generally, without restricting the disclosure herein as any other ways of specifying the collimator settings parameters are also envisaged herein. Such alternative collimator settings parameter formats may not necessarily be translated into such lines in all embodiments. However, a specification by the user via the user input device UID, in particular when GUI-based, in terms such lines is specifically envisaged herein in embodiments. In alternative embodiments, if the specification is not in terms such lines, suitable middleware may be used to translate such parameters into a respective set of collimator lines which are then supplied as input to the system USYS. Native processing of alterative formats is also envisaged in alternative embodiments.

Figure 2C:
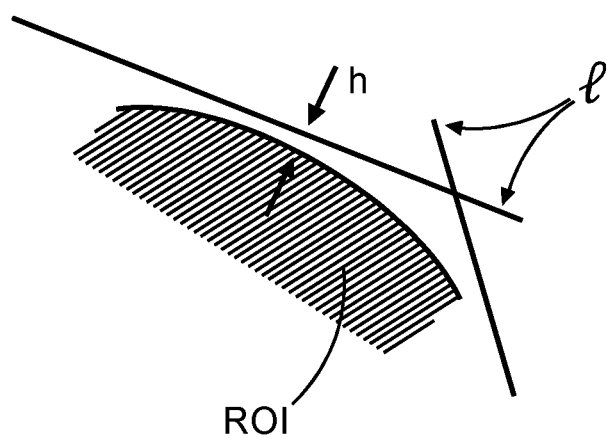

FIG. 2C) affords a detailed representation of a collimated field of view to illustrate the concept of tightness of collimation. Tightness of collimation refers to the clearance or distance h that remains between a collimator line, and the structure of interest or region of interest ROI as indicated hatched in FIG. 2C). The smaller the clearance h in at least one portion of the region of interest, the tighter the collimation is. In extreme cases, at least one of the collimator lines forms a tangent to the region of interest, as captured in the geometric structure in the image as recorded by detector D.

The plane of the drawings in FIGS. 2B), C) is that of the detector D. FIG. 2B) may thus be interpreted as portions of an actual projection image acquired by the detector in that plane. Given the remaining imaging geometry settings, in particular the magnification (the distance between x-ray source XS and detector plane D), a specification of the lines in the detector plane suffices to uniquely define a collimator setting for one or all of the collimator blades. That is, given a current set of imaging geometry settings, the computed complemented collimator settings, when provides as a set of such lines, can be translated by middleware into a corresponding set of commands to drive the actuators AC to so effect the computed collimator setting l'.

It is hence envisaged in embodiments herein that the user may merely indicate on a touch screen for example, a single (or more) collimator line or a section thereof, by specifying a single or plurality of parameters in any vectorial (x,y) or parametric representation. For example, an angular representation may be used, or other. For instance, user selects a single geometrical point on an image. The orientation of the collimation line may be perpendicular/parallel to one of the predefined image axes. In another example, user provides two geometrical points, which are collinear with the collimation line. In yet another example, user provides single geometrical point, and initially suggested orientation is adapted by changing the orientation angle. Alternatively, specification is by the user executing a lineal figure gesture for example. The touchscreen may display a current image or other representation of the current FOV. The (geometrical) line so specified may then constitute a partial collimator setting l which can be processed by the proposed system USYS to compute the complementing remaining, such as three other detector lines, to provide a complete set of collimator setting parameters l', which can be used to drive the actuators to effect the corresponding collimation.

In addition or instead to specifying merely one collimator line or a portion of that line, the said section thereof, the user may also specify in broad outlines at least part of the region of interest. These two information items, the geometrical region of interest and at least one collimator line may be used by the system USYS to compute in embodiments a full set of parameters l' that can be used for a complete collimator adjustment.

The complemented collimator settings may be displayed graphically on the display device DD, UD, overlaid as an overlay-graphic on the current image. It is only the computed, the completing parameters l*, that are so displayed, or it is the total set l'=l∪l* that is displayed.

When specifying the region of interest as an optional parameter as described it may not be necessary for the user to fully circumscribe the region of interest. This is because, in embodiments, the current image has been pre-segmented by the system USYS into segment structures, and the user is merely required to identify, by as little as a single point, such as by touch screen action, the desired segment that represents the desired ROI. The at least partial ROI specification, together with a partial collimator line, or section thereof, suffices therein to compute the complemented collimator setting parameter l'. More importantly, as proposed herein, by specifying not only the region of interest and the collimator line or section thereof, a clearance estimate δ between the two is defined. This clearance estimate may in embodiments interpreted by the system as an indication for the desired collimation tightness h. The estimated collimation tightness will then be automatically applied to the remaining collimator lines to so define the complete collimator setting l' having the requisite tightness h. In yet other embodiments, the user merely specifies a measure for the collimator tightness, such as a normalized value such as between 0 and 1 for example, instead of specifying a collimator line or section thereof. Based on this collimation tightness measure, the complete collimator setting parameters l' are computed by system USYS. In embodiments, collimation tightness parameter δ is estimated from user input and either predicted segmentation mask or predicted heatmap. For instance, h can be estimated by calculating a perpendicular distance between the collimator line, and the closest feature with the highest activation value (e.g. value 1 in the segmentation mask, see for example FIG. 6), where in other words h=0. Collimator tightness will be explained in more detail below at FIG. 6.

The proposed system USYS thus is not only computing the complete collimator setting l', but is also capable of detecting a user preference, namely the desired collimation tightness implicit in the provided user input. This further allows facilitating operation of the imaging apparatus IA as the requisite collimation tightness may be down to user preference and may hence differ from user to user. This may be important in clinical settings where multiple users are to use the given imaging apparatus IA. In addition, during a given medical procedure the requisite collimation tightness may change. One part of the procedure (such as an intervention) may call for a very tight collimation, whereas in other parts of the procedure a more relaxed collimation regime is more appropriate.

In addition, as is proposed herein in some embodiments, the collimator setting is adjusted in real time dynamically in response to changes of other aspects of the imaging geometry of the imager IA. For example, an event handler (not shown) embedded in the system USYS intercepts control commands directed to other aspects of the imaging geometry, such as angulation, table position/height changes etc., as described above. Once the event handler intercepts such data indicative of the intended imaging geometry change, this data is forwarded to the system USYS and processed so that the current collimator setting is adapted to correspond to the new field of view as a result of the imaging geometry change. The intercepted data is likely generated at user interface elements at the console CC. For example, such signals may be generated by the joystick or other UI element operated by the user to request an other-than-collimation-imaging geometry change. Preferably, in this embodiment, the same collimator tightness as per the current collimation setting is maintained and applied to the new FOV, and no further user input in terms of collimation parameters is required. In another example, collimator tightness changes together with the imaging geometry (any one of view angle, magnification factor, etc) to account for expected apparent drift of the anatomy of interest. If this fully automatically proposed new collimation setting is not to the user's liking, the user can again provide partial user input as described above. The system USYS will thus compute new/updated missing collimator setting parameters parts l*, to compute a full set of collimator setting parameters l' for the new FOV, which are then applied automatically or displayed first, as desired.

Figure 3:
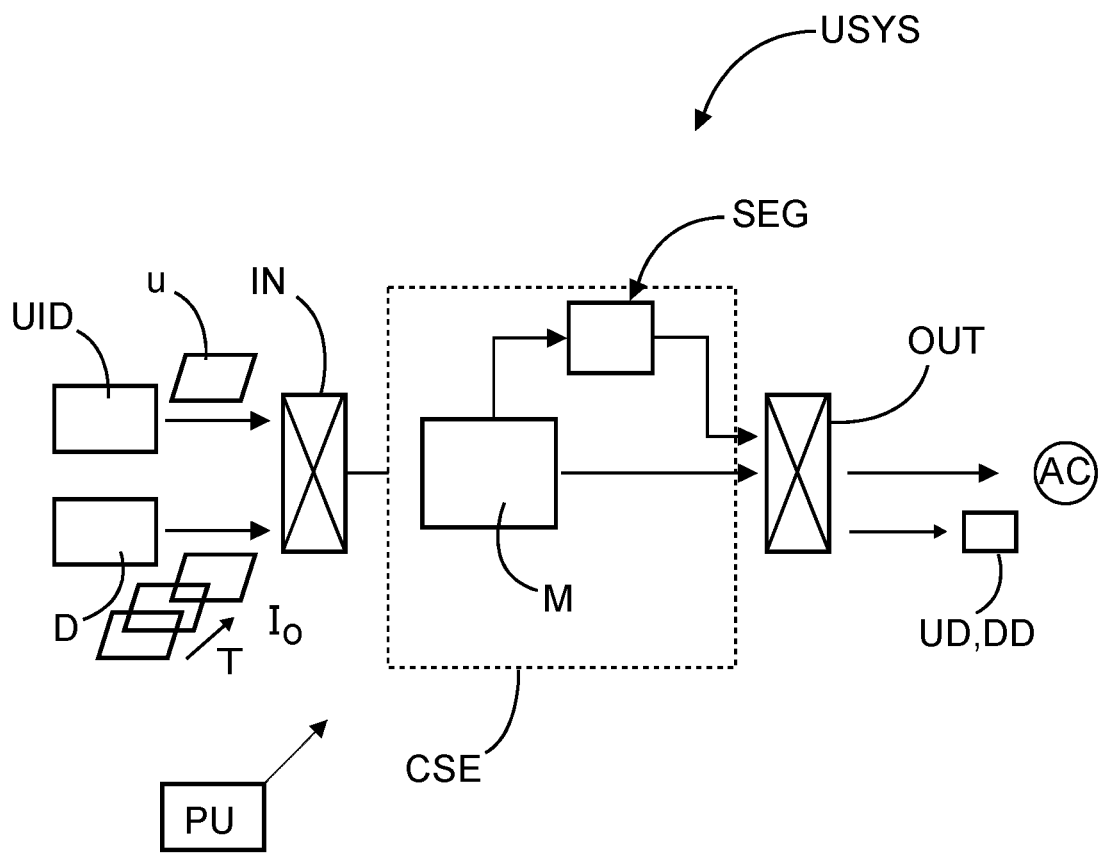
FIG. 3 shows a schematic block diagram of a computer implemented system for facilitating collimator adjustments.

Reference is now made to the block diagram of FIG. 3 which shows more details of the proposed user system USYS. As proposed herein in preferred embodiments, the system USYS is implemented by using machine learning. In particular, the system may comprise a machine learning model M, trained or pre-trained on training data as will be described in more detail below.

Assuming for now the system has been trained sufficiently with its parameters adjusted, in deployment, the phase after training, and one or more input interfaces IN of the system USYS receive user input u as supplied by the user through the user interface device UID.

The user input u may include, as described above, a merely partial specification of the intended collimator setting parameters l. The user input u may include one or more line sections of a collimation line. More than one (but preferably not all) collimation lines may be included in the user input u. In addition or instead, no collimation line is supplied but other parameters that are suitable to specify the intended collimator settings. For example, the user supplied collimator settings parameter may include a quantification of the collimator tightness clearing δ as illustrated above with reference to FIG. 2C). Optionally, the currently captured x-ray projection image $I_0$ as recorded by the detector D in the current detector plane is also received at interface IN. As described, the user input may further include a partial or complete specification of the intended ROI in respect of which the user may wish to collimate. The user input may include one or more collimation or shutter positions generated via existing interfaces (TSM or TSO) or via other interfaces (gesture, eye tracking, voice, AR, etc.).

The user input u, preferably with the current image $I_0$, are then processed by a collimator setting estimator CSE to compute the complemented or improved collimator setting from the provided input data. To do this, the collimator setting estimator CSE includes the trained machine learning model M to which some or all the input data u is applied. In some embodiments, the intended completed or improved collimator setting parameters l' are computed end-to-end by the machine learning model M itself. In order words, all the computations are done by the machine learning model M, but this may not be so in all embodiments as will become apparent further below when discussing other embodiments.

As will be discussed in more detail below, the machine learning model M may be arranged as an artificial neural network in various architectures. Preferred types of architectures comprise computational nodes arranged in a sequence of layers. In end-to-end embodiments, the intended output is regressed into a regression result. The regression results represents the intended completed improved estimated collimator setting parameters l'. In particular still, the regression result is supplied by a final layer of this model M. The user input is processed by the machine learning model to extract the user preferences for the intended collimation setting as embedded in the provided user input and/or the current input image $I_0$.

However, such an ML-based end-to-end embodiment is not required in all embodiments. Specifically, in alternative embodiments, machine learning is still used, but it is instead internal data, produced in a hidden layer of the machine learning model that is processed by a further component of the estimator CSE to obtain the result. Rather than using data supplied as final output at output layer as done in the end-to-endo ML embodiments, in non-end-to-end ML embodiments it is intermediate data that is harnessed. This internal, intermediate data may include feature maps. Such feature maps are representative of more latent abstract patterns which the model has been able to extract from the input data. Because of its nature, the internal feature map is produced by the given hidden layer as output of an activation function that is part of the given hidden layer. Feature maps may represent a distribution of a variety of features in image domain in feature space, as an abstraction of image content.

In some of the non-end-to-end ML based embodiments, the feature map that is segmented. Specifically, it has been found that the features maps are more robust against certain specific individual peculiarities of the input data or imagery $I_0$. It is therefore this feature map that is processed in embodiments by a computational component different from the model M to obtain the complemented collimator settings l'. In embodiments, the feature map may be reformatted such as by re-sampling to correspond in size to the current image $I_0$. For example, the feature map φ, resampled or not, may be processed in embodiments by an analytic image segmentor stage SEG. Image segmentor SEG does not necessarily use machine learning methods. More particularly, in embodiments, no prior training data was used to train the segmentor SEG, although ML-based embodiments of the segmentor SEG are also envisaged. Some feature maps may be color-coded with hue, saturation or brightness and it is the so color-coded feature maps that are processed, and optionally displayed. Non-ML type segmentors envisaged herein include feature based detection such as SIFT or other transforms, or as simple threshold-based segmenting, segmentation using color spaces (hue or saturation, or pixel intensity), region growing algorithm-based segmentation, etc. Analyzing or segmenting feature maps for computing the missing collimator setting parameters allows one to better capture the intended user preferences in terms of desired collimator settings. Some embodiments of ML based segmentors SEG envisaged herein include deep learning segmentors SED, such as those in U-Net architecture, Mask R-CNN and their variants, as well as other preferably fully convolutional artificial neural networks. If color-encoding is used, the segmentor SEG that operates on the feature maps or heat maps may use color/hue/saturation rather than edges or pixel intensities as in other types of segmentation (also envisaged herein in embodiment without color encoding).

More broadly put, the machine learning model is a transformation that involves three different spaces: i) the input space which may include the image space as represent by current image $I_0$, ii) feature space, and iii) collimator parameter space. In end to end ML embodiments, the result is computed by transformation from input space via feature space to collimator parameter space. In non-end-to-end ML embodiments, ML is merely used to perform a transformation into feature space. In such non-end-to-end embodiments, feature map(s) in feature space is accessed by the additional computational component, such as the segmentor SEG. The accessed feature map is processed by the additional computational component into the sought collimator parameters in collimator parameters space.

In either embodiments, end-to-end ML or non-end-to-end ML, the computed collimator setting parameters l' is/are output at output interface OUT. As mentioned earlier, the output result l' can be used to automatically drive actuators of the collimator to apply the desired estimated collimator setting. In addition or instead, a graphical rendering, for example in terms of a system of collimator lines, may be displayed on a display device UD, DD. A visualizer VZ component may produce a graphical overlay of the graphical rendering of the result l' which is overlaid on the current image $I_0$. In yet other embodiments, the collimator setting parameters may be stored in a database so as to prepare events logs for regulatory purposes, or the collimator setting parameters may be otherwise processed.

Figure 4:
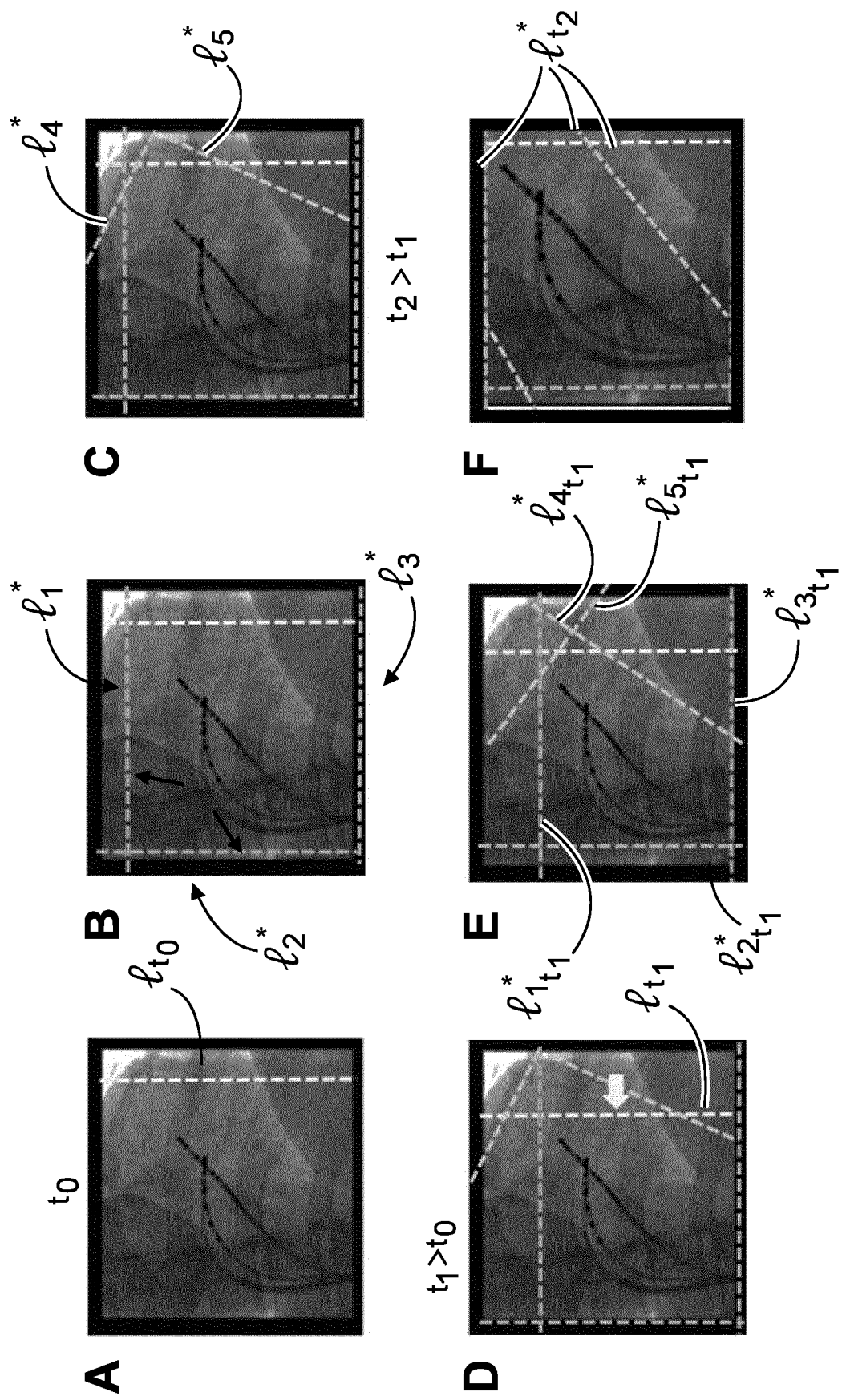
FIG. 4 shows an illustration of operation of the system of FIG. 3 in embodiments.

Reference is now made to FIG. 4 which illustrates operation of the proposed system at different time instances t0, t1 and t2 during an intervention in which imagery is acquired by the imaging apparatus with changeable imaging geometry.

At initial time $t_0$, a current frame $I_0$ is acquired. A user specifies partial collimator setting parameters l, for example by touch screen action. For example, the user may specify, out of the four possible lines, merely one single collimation line, referred herein as $l_{t_0}$. As a response thereto, the remaining complementing collimator lines $l^*=l_{1-3}$ are then computed by the system using the machine learning component M as described above in FIG. 3. A complete collimator setting, including the user provided one $l_{t_0}$ and the computed ones $l_{1-3}$ may be displayed as shown in pane B on the current $I_0$. The complete set of collimator parameters $l_{t_0}$, $l_{1-3}$ may be used to drive the actuators AC to effect the collimator setting corresponding to those parameters.

Additionally and optionally, as shown in pane C, the collimator setting may also comprise settings of wedges, shown as oblique dashed line in pane C, whilst panes A-B refer to shutters. At a later time $t_1 > t_0$, the user may decide to change one (a single one) or more parameters of the current collimator setting parameters. This is illustrated in pane D, by the user changing the earlier specified collimator line $l_{t_0}$, for example by shifting same. This is illustrated in pane D by the user shifting the collimator line to the left. A drag-and-drop touch screen finger gesture operation or a computer mouse operation may be used in examples to implement this option.

In response to changes to one (or more) of the current collimator settings, the remaining collimator parameters are adjusted accordingly as shown in pane E. If more than one lines are changed, this can be done in concurrently or sequentially.

Pane F illustrates the situation where at a yet later time $t_2 > t_1$, the current imaging geometry is changed for example by magnification or re-orientation of the gantry, etc. In response to the request for changing the other-than-collimator-imaging geometry, the collimator settings are adjusted to follow the region of interest dynamically, preferably without any further user input. Then, later, once further user input is received in respect of the collimator, collimator tightness and/or the remaining collimator setting parameters are then re-computed as in panes A, B.

Figure 5:
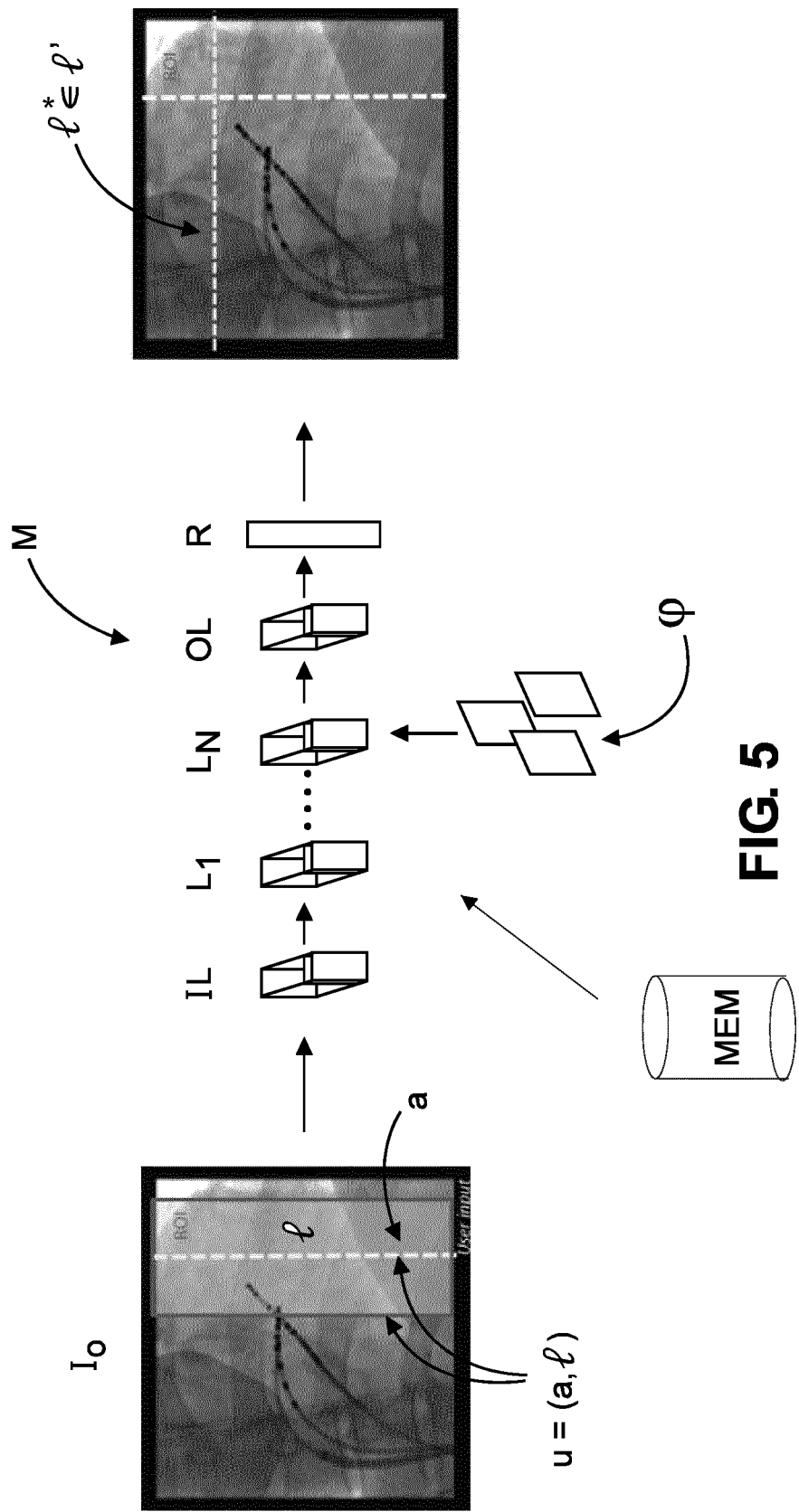
FIG. 5 shows an architecture of a machine learning model as may be used to implement the system in FIG. 3.

Reference is now made to FIG. 5 which shows a block diagram of a machine learning model M as may be used by the system USYS in embodiments. FIG. 5 is an embodiment of the end-to-end ML variant. Specifically, FIG. 5 shows a block diagram of a machine learning model in an artificial neural network type architecture.

Preferably, a convolutional network CNN is envisaged herein. The network may be fully convolutional or may be partially convolutional and may include one or more fully connected layer. Alternatively, the whole network is fully connected. Some or all or the layers may be recurrent. Additional recurrent layers may be included. The left portion of FIG. 5 illustrates the user input u comprising an optional region a, and a partial collimator setting parameter l. The network may be feedforward as shown, but may instead be recurrent.

The user input may be provided through a GUI. A current image $I_0$ or a sequence of images is displayed, and the user specifies one or more (but preferably not all) intended collimator lines. In addition or instead of specifying the collimator lines, a collimator tightness h is selected by user, such as by specifying a scalar value in a predefined range, one end of the range indicative of tight/tangential collimation, the other end of range indicative of a more permissive collimation at a given maximal distance from the ROI. Optionally as mentioned, the intended region of interest a is specified by outlining, or by merely indicating one or more points to define the region of interest. Preferably, the collimator line intersects, or is at least tangent to, the ROI. In this manner, the indicated line has a dual function as it indicates at least a section of the collimation line and the ROI. The region of interest may be specified on a single input image or on a sequence of images (the frames). Such a sequence of frames, a video feed, may be generated in a fluoroscopic imaging operation specifically envisaged herein in embodiments.

The input data u is provided in a suitable format, such as in vector or matrix format. The input data preferably includes in input image and the one or more collimator lines designated therein but a pointer tool, touch screen action, or other. The input data is received and processed at input layer IL of neural network M. Output of the input layer then sequentially passes through the network. The data is processed by one or more hidden layers $L_1$-$L_N$, and is then finally regressed into a regression result R by the output layer OL. The regression result R represents the estimated complemented collimator setting parameters. The output may be provided as a system of coefficients $(a_i, b_i)$ that describe a system of geometrical lines, such as 4 or more lines to represent the complete set of collimator lines. For example, a system of 6 set of coefficients $(a_i, b_i)$, i=1 . . . 6 may be provided to define the collimator lines for 4 shutters and 2 for the wedges. The a's are the x-intercepts and the b's are the y-intercepts. Some collimator lines for blades without rotational capabilities, such as wedges, may be described by a single coefficient b. If blade is rotatable, a reference orientation maybe defined. For example, orientation may be assumed to be orthogonal to one of the image axes. Thus, the regression result comprises the complemented collimator setting parameters. In particular, the complemented parameter comprise the one or more lines that were missing in the incomplete input data. The complemented lines are shown diagrammatically as the predicted line l' on the right portion of FIG. 5. Thus, FIG. 5 is an illustration of an example of a deep neural network that, given an image ROI extracted from an input parameter (e.g., user interaction with one collimation variable) predicts the other collimation setting parameter. In the example of FIG. 5, the right collimation line is used to predict the top collimation line.

The input and hidden layers OL, $L_1$-$L_N$ preferably include non-linear activation functions, such as ReLu(x), or arctan (x), sigmoid, or other, whilst the output layer OL may or may not implement such non-linear activation functions. However, as the image size is known, using such non-linear activation functions to constrain output at layer OL to a finite known interval, say the unit interval is advantageous. The slope of the activation function defines a smoothness (on which more further below. As opposed to activation functions such as ReLU in the hidden layers, activation function of the output layer defines the task that the network performs (such as regression, etc).

Feature maps φ are produced whilst the data propagates through the network $L_1$-$L_N$. There is preferably no feature map produced by the output layer. At some or each hidden layer, one or more feature maps are computed. The feature maps may be computed by passing respective logits to the activation function at that hidden layer or any other hidden layer. The logit is the result of processing, by a convolutional operator or other operator for which the given hidden layer is configured for, the feature map from the earlier, preceding layer. The activation function is applied to the logit of this hidden layer to compute the feature map for that hidden layer. This feature map is then passed on the next layer, and so forth. The preceding layer is either another hidden layer or the input layer. In this manner a sequence of generations of features maps are generated, the generations growing with layer depth. In general, the number feature maps per layer is also growing with depth, as a given layer may implement plural operations, such as different convolutions, and that number is in general growing with layer depth.

One or more of the feature maps at a given hidden layer may be processed by segmentor SEG or other computational component as mentioned above in the non-end-to-end ML embodiments as will be discussed shortly below.

Specifically and preferably, a deep convolutional neural network is used. The depth is largely a function of the number of hidden layers, or, in recurrent networks, on the number of passes through hidden layers. The network M in FIG. 5 may include a single or plurality of intermediate/hidden layers. The number of hidden layers, the depth, may depend on the complexity of the application or availability of the training data.

Each layer may contain any one or more the following operators: convolution operator, batch normalization operator, dropout, and pooling. Each hidden layer, and in embodiments the input layer, but preferably not the output layer, includes an operator to implement the non-linear activation function. As the data propagates through the network, multi-dimensional feature maps—or a sequence of feature maps—is generated by the hidden layers. The output layer OL converts the one or more feature maps into a single or a sequence of low-dimensional embeddings. Global average pooling or map flattening techniques may be used in the output layer, followed by a regression layer. A sigmoid activation function or other non-linear activation function may be applied to the output from the regression layer in order to constrain the output parameters, as mentioned above.

There is usually a plurality of feature maps at a given depth and/or across the network depth. Preferably, the last layer (before the output layer OL) is accessed by the segmentor SEG for segmenting as explained above. However, feature map(s) of any hidden layer may be accessed instead. Feature maps located deeper ("distal" from input layer IL) in the architecture M are preferred. This is because the more distal the layer, the more abstract or complicated structures of the underlying task it encodes.

Figure 6:
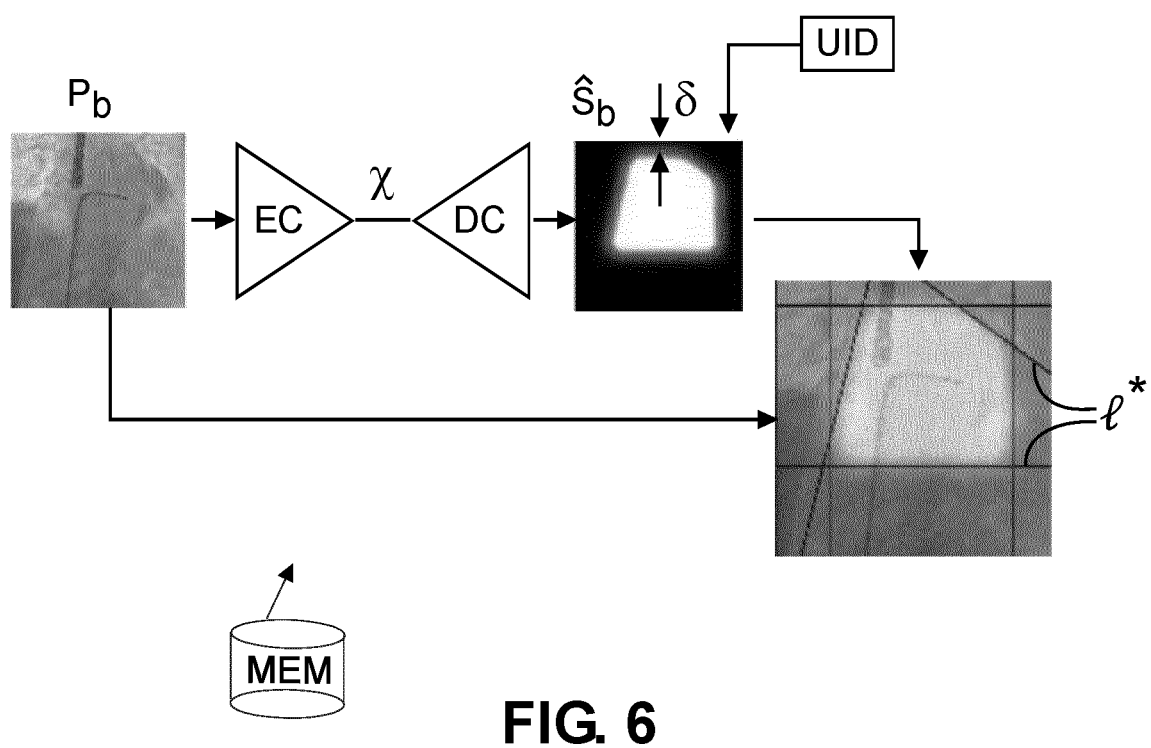
FIG. 6 shows another embodiment of a machine learning model of the encoder-decoder type that may be used to implement the system in FIG. 3.
Figure 8:
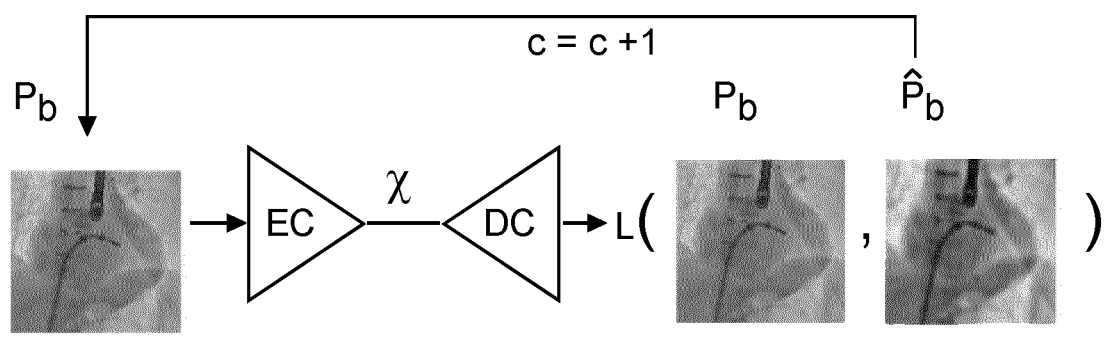
FIG. 8 is yet another embodiment of a machine learning model of the autoencoder type as may be used by the system of FIG. 3.
Figure 8:
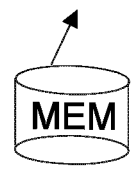

Reference is now made to FIG. 6 which shows a block diagram of a machine learning model M for embodiments of non-end-to-end ML implementation. In this embodiment, a single image $I_0$ or a plurality of x-ray images are applied as input u=$I_j$ to the input layer and are propagated through the layers. As described above, feature maps are generated in the hidden layers and/or at the output layer OL. The output layer OL may be a regression layer. In this embodiment, feature maps are separately processed (by segmentor SEG or other entity) outside the machine learning model M in which they are generated. This is in contrast to the end-to-end ML embodiments, where feature maps are not so processed but are instead processed all the way through to the output layer. At the (final) output layer OL, the feature maps are combined into the regression result such as for example in the model M of FIG. 5. Whilst this type of feature maps based processing may also be implemented in the network shown in FIG. 5, in preferred embodiments an autoencoder ("AE") type network is used as diagrammatically shown in FIG. 8. In another embodiment, an encoder-decoder (EC-DC) type network may be used as diagrammatically shown in FIG. 6. In FIGS. 6 and 8, the turned triangle symbols "▷" and "◁", each represent a sequence of one or more hidden layers that use operators to produce intermediate outputs (logits) having their dimension and/or sparsity decreasing and increasing with network depth, respectively. Whilst the (one or more) input image was optional in the ML model of FIG. 5 above, providing such one or more images as input is preferred for the embodiments of FIGS. 6 and 8.

Turning now first in more detail to the encoder-decoder type networks, all that has been described above for network of FIG. 5 is of equal application, except that the output from the network of FIG. 6 is a feature map rather than a set of regressed parameters. In an encoder-decoder setup, the input image is first transformed into a lower dimensional representation χ by an encoder component EC of the encoder-decoder network. This lower dimensional and/or smaller sized representation is referred to herein as the "code". The code χ is then up-sampled by a decoder DC component, arranged in series with the encoder EC, so as to increase the dimension/size of the central representation, so that, eventually, the dimension and/or size of the output image matches the dimension and/or size of the input image. The "code" thus "encodes" properties or structures of the input image in a compact form so that, whilst reduced, is still capable of being decoded back into the input image. The terms "size/dimension" refer to the number of entries in the data structure of the feature map or input/output image and/or the vector length of the set of indices to localize such an entry. For instance, a matrix (eg, an image) with pixels 50×50 has a larger size than an image 40×40 or 50×40. But both have the same dimension. A three-channel image 50×50×3 has a larger dimension (3D) than a 2D image at 50×50. Because the 3D image also has more data points, it is also larger in size. There are also embodiments of the encoder-decoder envisaged, where the encoder EC generates code of larger size and/or higher dimension than that of the input image to foster over-complete representations. In this alternative embodiment, the encoder EC may produce the code at a larger dimension and/or size, but at a higher sparsity. In particular, regularization mechanisms and special cost functions may be used to promote over-complete and sparse codes. The encoder portion may include multiple hidden layers, each implementing convolutional operators and preferably an activation function to be applied to the output of the convolution. The stride or the step width of the convolution operator may be larger than 1 to effect the reduction in size/dimension of the features maps. The decoder DC may include a number of hidden layers that implement operators to enlarge size/dimension. Transposed convolution operators may be used that essentially act as an inverse operation to the convolution caused by the convolution operators in the encoder EC. Whilst the convolution operator maps, initially, from pixels to features of progressively higher level, the transposed convolution operation maps features back down to pixels and/or feature of lower level. Hidden layers in the decoder DC may also implement activation functions. Functionally, the deconvolution operators can be formulated in terms of convolution operations which are then summed. See for instance section 2 in M D Zeiler et al in "*Adaptive Deconvolutional Networks for Mid and High Level Feature Learning*", 2011 International Conference on Computer Vision, Barcelona, Spain.

Turning now in more details to feature maps, these may be scaled in size to correspond to the size of the input image $P_b$. It can be seen that thanks to the activation function outputs which are used to compute the feature map, smooth border portions of segmentations in the feature maps are obtained. This smooth border effect is due to a class of activation functions envisaged herein that are not configured for hard-thresholding typically used in some segmentation CNN architectures, but instead may map non-linearly albeit smoothly into a limited range such as the unity interval [0,1]. Some such smooth activation functions have an S-shaped profile with slope approaching zero towards either end of the range and with a maximum slope such as around 1 at a given position (such as 0.5) in the range. Said position is referred to herein as the threshold of the activation function. Thus, in the feature map, values vary from 0 to 1 to define locally the smooth border portion of natural segmentations encoded in the feature map. These segmentations may emerge in a given feature map during processing of the input data by the network M. The in-feature map segmentations present the earlier mentioned learned latent pattern in the input data. A network may include multiple feature maps per hidden layer and there may be multiple such hidden layers. Preferably the last feature map from the decoder DC is used. Alternatively, any feature map at any hidden layer in the decoder DC path may be used.

In encoder-decoder type embodiments as in FIG. 6, an output from the final layer of the decoder stage DC may be preferably used as the feature map in which to segment for the sought after collimator setting parameter(s). It may not be necessary however to necessarily use a feature map from the last layer for the decoder DC, as feature maps from earlier, upstream layers of the decoder stage DC may also be used once they are resized to match the dimensions of the input. Preferably those earlier (or later) feature maps are within k=3 layers of the last decoder layer.

The smooth border portion in an example segmentation is indicated as 6 in FIG. 6. The smooth border portion may be used in this embodiment to compute the complementing collimator setting parameters l* as indicated on the right side portion of FIG. 6. Whilst as in previous embodiments the user can may still specify one or more collimator lines for example in the segmented feature map, this may not necessarily be required. Instead, an indication of the desired collimation tightness is specified by the user in respect of one segmentation segment in the feature map, such as the last feature map from decoder path.

Specifically, in the border portion 6, the user may merely define a point. This will then correspond to an activation function output value, and this value may then be used by the estimator CSE as an anchor point to construct an isoline in the feature map. The isoline then directly defines a collimator curve for the intended collimator setting. The collimator curve may be broken up into a system of approximating lines to so obtain the system of linear collimator lines as referred to earlier. However, such as beak up into lines may not always be required such as for multi-leaf collimators as may be used in radiation therapy. Such multi-leaf collimators allow defining FOV shapes that are better approximated by collimator curves than lines. Thus, the specification and/or output format for the computed complemented collimator setting parameters as envisaged herein is not confined to lines but could be any curve, such as a higher order polynomial. A piece-wise defined system of linear and non-linear curves is also envisaged herein in embodiments. The isoline embodiment may be advantageously used in radiation delivery devices, such as in Cyberknife® systems or others, where collimation to lesioned tissue of complex shapes may be required.

As an alternative to the above described selection of a point in the border portion of a feature map segment, the user may adjust, by a slider or other suitable user interface, touchscreen etc, the threshold of the activation function itself. With each adjustment, the feature map is recomputed with the effect of producing border portions with varying levels of smoothness. By segmenting the feature map for the edges of a segment having an adjusted level of border smoothness, the collimation tightness may be controlled. Segments in the feature map may be interpreted as a collimation mask.

The neural network used for the feature map extraction as per FIG. 6 is preferably a deep fully convolutional network. Any NN model suitable for segmentation tasks may be envisaged herein, such as U-Net, R-CNN, Mask R-CNN. If the network has an encoder-decoder architecture, preferably the last convolutional layer of decoder DC has a sigmoid activation function applied to values of the last feature map.

In any of the above described feature map based processing, a heatmap may be used instead. A heat map is a special type of feature map obtained by post-processing a feature map. The post-processing to derive the heat map may include weighted summation followed by non-linear activation. The heatmap may be displayed for control purposes to highlight an area of interest. Generation of heatmaps will be explained in more detail below at FIGS. 8,9.

It will be understood that the described encoder-decoder set-up in FIG. 6 may also be used in conjunction with the machine learning model depicted on FIG. 5. In this embodiment, feature maps produced by the network from FIG. 6 is used as an input to the network from FIG. 5, instead of the input image $I_0$. The regression output as supplied by the last layer OL from the network from FIG. 5 generates collimator setting parameters.

Figure 7:
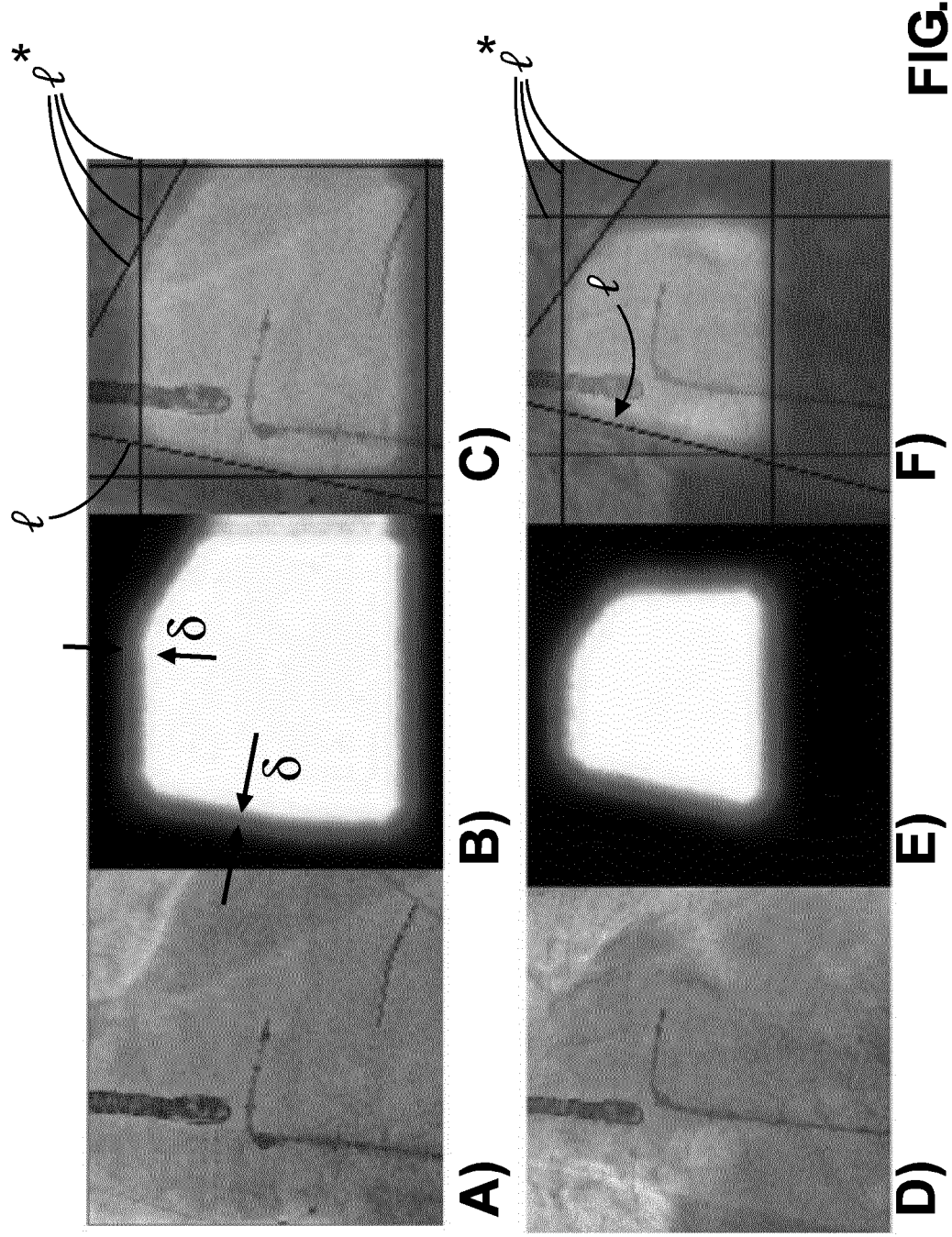
FIG. 7 is an illustration of the results obtainable by the system using the machine learning model of FIG. 6.

Reference is now made to FIG. 7 which shows an illustration of results obtainable by the EC-DC-type based ML system discussed above, specifically in FIG. 6. FIG. 7 illustrates results on selected fluoroscopic x-ray images from a mitral clip deployment procedure. Starting from the left, each row A-C and D-F shows respectively: input images, proposed collimation masks, suggested positions of collimator lines for wedges (orthogonal lines) and shutters (oblique). User can adjust the suggested positions by adjusting the activation threshold, say from 0 to 1, or by picking a value in the border portion, with computation of the collimator lines as isolines as explained above.

An encoder-decoder type network is trained in a supervised way. At each training iteration an input image is fed into the network and predicted by the network "soft" collimation mask—last feature map from the decoder DC path—is compared to a ground-truth collimation mask using a predefined loss function. An example of loss function is a mean-squared error (MSE) or cross-entropy loss. Parameters of the network are adjusted automatically based on the difference calculated between the ground-truth collimation mask and predicted mask. Parameters that are adjusted include the weights and the biases of the intermediate layers. During training process the value of the loss is minimized and stopped when certain stopping criteria are met. Ground-truth collimation masks are provided by the expert users, such as physicians.

Reference is now made to FIG. 8 which shows another embodiment of a non-end-to-end ML based implementation, using an auto-encoder set-up similar to the one described above at FIG. 6. The model is preferably a deep, fully convolutional network. Preferably but not necessarily, feed-forward architecture is used.

Auto-encoder type networks are preferred over the likes of FIG. 6 as AE-type networks can be trained in an unsupervised manner. The learning objective for autoencoder is for the decoder to replicate at its output the encoder input to encode the structures in the underlying data i.e. to extract robust feature maps. Unsupervised learning schemes other than AE-based are also envisaged herein. If a supervised set-up is used in some alternative embodiments, the learning objective may be arbitrary such as classification of image objects. Preferably, the supervised learning is based on applicable imagery such as x-ray projection images that show a fair distribution of image objects, such as footprints of organs, organ parts or medical tools/devices such as catheters etc, that may be reasonably expected to feature and be used during the interventions for which the proposed collimator setting is intended. As before, the system is trained based on input data to replicate, at the output of the decoder DC stage, the input received at its encoder stage EC. As in embodiment of FIG. 6, a single x-ray image $I_0$ or a plurality of x-ray images are applied as input $u=I_j$ to the input layer and is/are propagated through the layers of the model.

Figure 9:
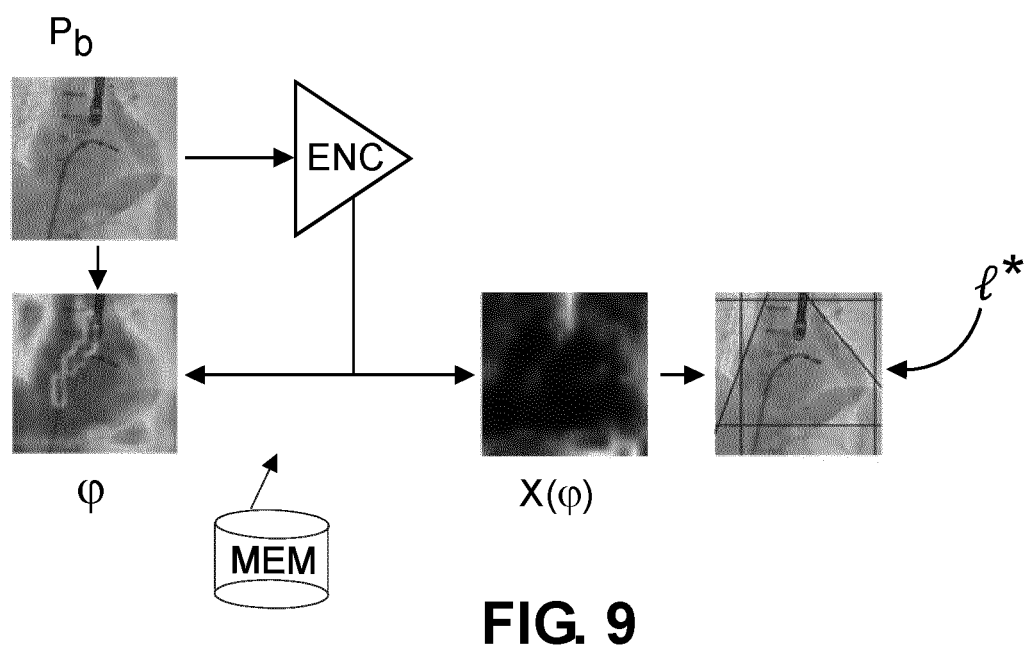
FIG. 9 shows a block diagram of processing steps in relation to the machine learning model in FIG. 8.

As described above, feature maps are generated in the hidden layers. The learning or training phase is based on an optimization algorithm. The optimization may be implemented in one or more iteration cycles i: i+1, during which a cost function L is improved by updating parameters of the AE-network. The cost function L measures a deviation between output $\hat{P}_b$ and the input $P_b$. Once the system in FIG. 8 has been trained sufficiently, the decoder part DC is no longer required as shown in FIG. 9, where only the encoder part EC is retained. As in all embodiments of any model envisaged herein, training may be a one-off operation, or may be repeated once new training data is available, at which the point the decoder DC stage is used again as in FIG. 8. Whilst most training set-ups as discussed herein are naturally formulated as an optimization where a cost function is minimized, this is not at the exclusion of dual formulation, namely a maximization of a utility function.

The trained encoder EC is now used as follows in deployment. A current image $P_b$ is applied and a feature map is produced in the encoder as the input image is propagated therethrough. After passage through a sufficient number of layers in the encoder, a suitable feature map p is accessed by the estimator CSE. For example, the code $\chi$ may be accessed as a special feature map, usually having the smallest dimension or being of highest sparsity. Feature maps p of upstream layers of the encoder EC may be accessed instead, and this is preferred especially when heatmaps are to be computed from such feature maps.

In embodiments, a feature extraction algorithm is then used by segmentor SEG to process the feature map, such as $\varphi=\chi$, so as to extract features $X(\varphi)$ to define segmentation segments. The feature extraction algorithm may be analytic (non-ML based) or ML-based. Any feature extraction algorithm can be used.

Specifically, in embodiments, segmentor SEG receives preferably a resampled feature map extracted from the last convolutional layer of the encoder EC subnetwork. The resampling operation is a dimension-reduction operation: a number of feature maps or a high dimensional features map is reduced to 1D or 2D for example. Resampling is typically applied to the feature map to ensure dimensionality match with the input size.

In autoencoder type embodiments as in FIG. 6, the feature map (the code $\chi$) as output by the final layer of the encoder stage EC may be preferably used as the feature map in which to segment for the sought after collimator setting parameter (s). Just like in the encoder-decoder setup in FIG. 6, it may not be necessarily the case to use a feature map from the last layer for the encoder EC, as feature maps from earlier, upstream layers may also be used, and so may be feature maps from the first or first few latter layers of the decoder stage DC. Preferably those earlier and later feature maps are within k=3 layers of the last encoder layer of code $\chi$.

In embodiments, instead of using a feature map, a derived feature map is used, referred to herein as heatmap. In general, a heatmap is a derived or differentiated feature map, whose values represent the relevance of a given feature map at a hidden layer for entries of the final output at output layer OL There are multiple approaches how the feature map can be extracted from the network's feature map(s), all envisaged herein. In some embodiments, a gradient-based approach is used to extract heatmap from feature map. In such embodiments, a differentiator of CSE calculates the gradient of the latent variable (code $\chi$) as output by the encoder EC with respect to one of the hidden (preferably convolutional) layer in encoder EC part of the autoencoder. The hidden layer is preferably the last layer before autoencoder code $\chi$ or any intermediate hidden layer in the encoder EC path. Weights calculated from the gradient-based approach for each filter output are hence obtained. The heatmap is then extracted by weighting and summing up corresponding filter outputs, followed by activation function such as ReLU or other to enhance or restrict certain values.

Alternatively, this may be done without weighting the outputs by simply applying a global average pooling or other cross-channel operation such as global max pooling followed by non-linear activation function. The results may then be normalized and may be optionally scale to desired size of the input image. Other methods such as the Grad-CAM method may be used, such as described in Ramprasaath R. Selvaraju et al, in "*Grad-CAM: Visual Explanations from Deep Networks via Gradient-based Localization*", 2016, published online as preprint arXiv: 1610.02391.

The segmentor SEG segments heatmap into one or more segments. Preferably, the segmentation operation may be based on similarity. Any segmentation method known in the art may be used, such as k-means pixel clustering, region growing, active contours, simple thresholding, or machine learning approaches based on U-Net, R-CNN, Mask R-CNN. Another segmentation approach also envisaged for the segmentor SEG in embodiments is to calculate one or more different descriptors ds (see FIG. 10D)) for some or each isoline of the heat map, for instance by calculating magnitude and direction of gradients at some or each point on the isoline, or based on intensity values in neighboring pixels, and others.

Based on the extracted features/image segments, the collimator setting parameters I' can be computed. Preferably this computation is interactive, that is, is based on user input l. The user specifies as before either the segments themselves individually, by for example, designating a single (or more) points within the respective image segment. In addition or instead, a desired collimator tightness clearing h is provided as explained above. In addition or instead, one or more (but preferably not all) collimator lines are indicated in respect of a given image segment. The lines may intersect the image segment of interest or may be tangent thereto. The line may be set to pass through the smooth border portion of the segmented feature map. The line thus not only specifies the image segment but also defines the collimator tightness as described above.

The predicted collimator setting parameters are proposed by the system using generated segments. For example, the system USYS may calculate several candidates of the tangent lines to each polygon defined by the contour of the segments to compute the complementing collimator lines. Each candidate represents a collimation setting line, and therefore is defined by a y-intercept (parameter b) and slope (parameter a). For instance, tangent point is a y-intercept, and slope is defined by a direction of the gradient at this point. Input provided by the user i.e. a collimation line settings will define a tightness of the collimation based on its proximity to one of the candidates. Remaining collimation setting lines are chosen based on the similarity to such proximal candidate using keypoint descriptors.

Figure 10:
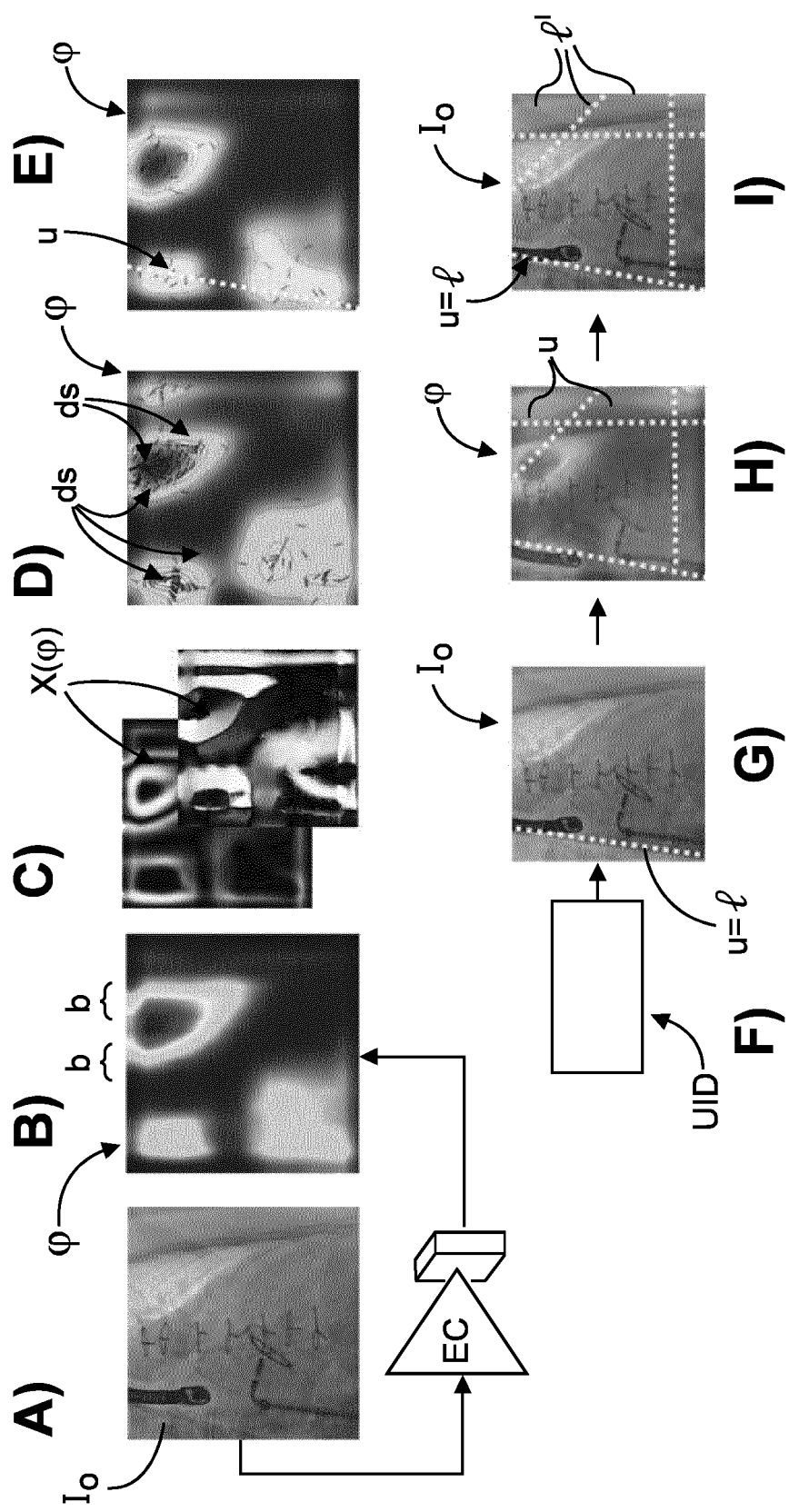
FIG. 10 is an illustration of a process flow of a machine learning model based implementation of the system in FIG. 3.

FIG. 10 is an illustration of the above described feature map based processing to compute the collimation parameters, based on a previously trained encoder stage of an auto-encoder set-up. An input image A), for example a currently acquired image $I_0$, is processed by the encoder stage EC to produce the feature map (φ B). The feature map, optionally rescaled in size to the match the size of input image, is now treated like and image that can be segmented C). The feature map may include segments b with smooth border portions. Gradient magnitude and phase or other features may be extracted D) from the feature map. The feature map may be processed in to a heatmap, and it is the heatmap that is processed in the following instead of the (original) feature map. Segmented segments of the feature map may be overlaid with keypoint descriptors ds calculated at either each location on the feature map, or each segment in the feature map extracted using e.g. k-means clustering algorithm or other algorithms know in the art (thresholding, region growing, active contours, color-based methods). Input u is provided E) by the user as a line (shown dotted), preferably intersecting the feature map at corresponding descriptors. The lower row F)-I) illustrates user scenarios. For example, user F) provides feedback, which may define a tightness level of the collimation. Eg, moderate collimation tightness is represented by a line far away from a region of interest, such as a projection footprint of a tool. In a higher tightness level, the provided line is closer to tool footprint for example. Wedge H) and shutter I) collimation lines are proposed and may be overlaid on either one or both of an augmented image and original x-ray image. The augmented image is obtained by blending the original x-ray image with the heatmap/feature map.

Figure 11:
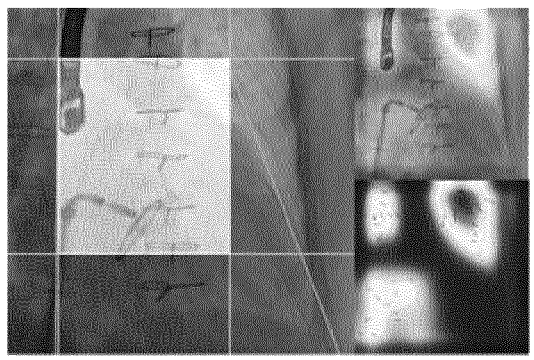
FIG. 11 is an illustration of results obtainable by the system in FIG. 10.
Figure 11:
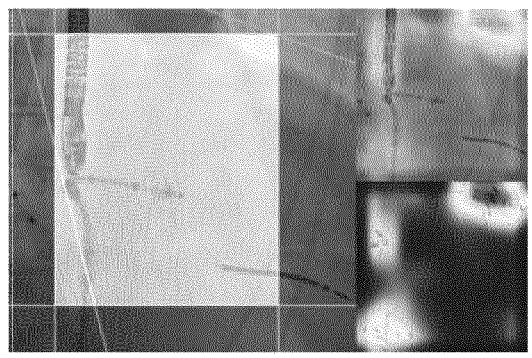
Figure 11:
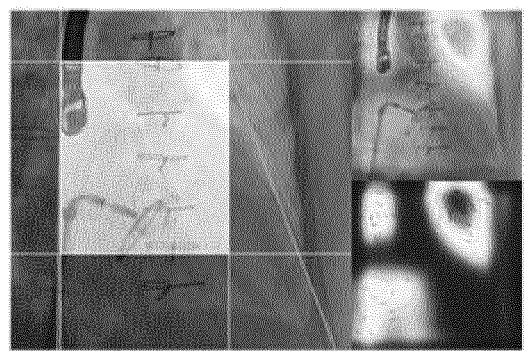
Figure 11:
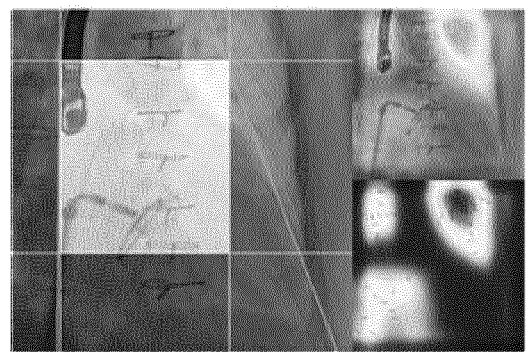

FIG. 11 is an illustration of results obtainable by processing feature maps of neural network architectures such as auto-encoders or others, for example as described above at FIGS. 8-10. The x-ray imagery represents mitral clip implantation procedures. A tight collimation is shown in the top row (A, B), whereas a moderate collimation is shown in bottom row (C, D).

It may be appreciated that predicting collimation parameters as per FIG. 5 might not be feasible from a small patch of pixel data (the ROI specification data "a"), especially when user input is inaccurate, or might be application specific. The feature map based embodiments in FIGS. 6-10 address this. The embodiments in FIG. 6 use a segmentation operation on the, preferably last, feature map. A possible drawback of this embodiment is that it requires ground-truth collimation masks. In the embodiments of FIGS. 8-10, a feature extraction is applied first to extract (rich) features from feature map, and the collimator setting parameters are based on the extracted features represented as feature maps. The embodiments in FIGS. 8-10 do not require ground truth, and may hence be trained in an unsupervised manner. Comparing the embodiments of FIGS. 6,8, one may summarize as follows. The FIG. 6 embodiments represents a segmentation network. The last (or other) feature map from the decoder DC is used to calculate the collimation lines. FIG. 8 embodiment represents a feature extraction network. Any intermediate feature layer at any hidden layer, typically from the encoder path (including code x) can be used to calculate collimation lines.

Figure 12:
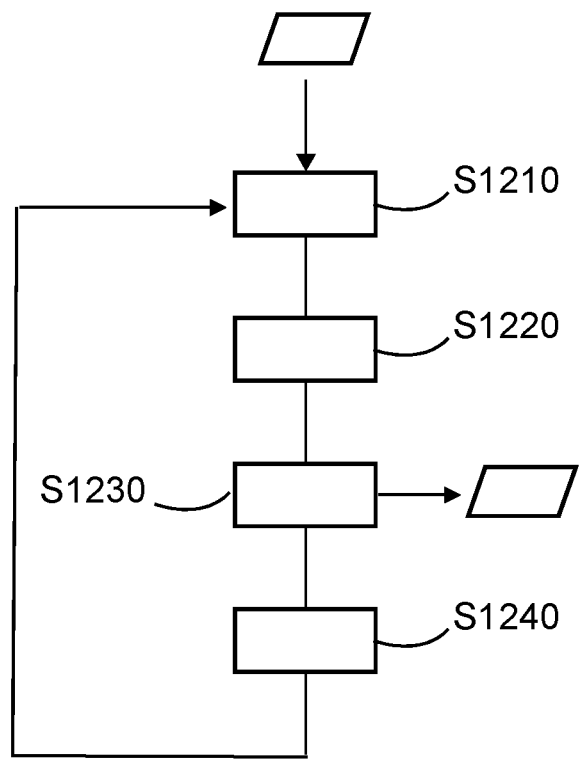
FIG. 12 is a flow chart of a method of facilitating adjustment of collimator settings.

Reference is now made to FIG. 12 which shows a flow chart of a method for facilitating collimator adjustments, preferably based on machine learning models as described above. However, it will be understood that the described steps below are not necessarily tied to the models described above. Any ML model can be used instead, end to end or non-end to end, optionally with feature map based extra processing with or without ML, as described above.

At step S1210, input data is received. The input data may include a current x-ray projection image and/or user supplied data. The user data is supplied by a suitable user input device such as a graphical user interface. The GUI may be touch screen based, or other. Alternative, the user data input data is generated by operation of physical actuators, such as buttons, joystick, levers, handwheels etc, preferably with encoded tracker, eye movement tracking, gesture recognition, etc.

The input data may comprises a collimator tightness parameter which may be a single number between 0 and 1, or in any other (bounded) range. In addition or instead, the input data includes preferably an incomplete description of a desired collimator setting. For example, the user input data may include a single or more collimator lines preferably less than the total number of lines required to fully specify the collimation setting. Any other input data equivalent or corresponding to such one or more collimator lines are also envisaged herein. The user input data such as the one or more collimator lines may be designated in the input image.

At step S1220, the input data is processed using a machine learning model pre-trained on training data. Step S1220 can be implemented end to end by the machine learning model, wherein the input data is fed into the model to produce a regression result at the final layer of the machine learning model that represents the desired collimation setting suitably complemented, improved or otherwise added to. Processing at the final layer does preferably not include processing with an activation function.

In addition, or in an alternative embodiment, rather than using the final result produced without activation at the final layer of the machine learning model, it is instead output of a hidden layer that is used at step S1220 to compute the complemented collimator setting parameters I'. The output is produced as a feature map of the hidden layer. The processing of the feature map may include using a non-linear activation function. The activation function at the give hidden layer is applied to a logit. The logit is obtained by processing, using other operations such convolution or transposed convolution or other, the output of an earlier layer.

In this feature map based embodiment, an analytic non-machine learning based segmentation algorithm may be used to segment the feature map or heatmap. The feature map/heatmap itself may be suitably scaled to have the same size as the input image received at step S1210. The segmentation may include extracting features from the feature map. The feature map is thus treated and processed like an image. The segmentation operation may be feature based, such as SIFT. The segmentation operation may result in individual segments in the feature map.

In such feature-map-based embodiments, it is the segments of the feature map (scaled or not) that are used to compute the complemented collimator setting parameters. In embodiments, once the segmented feature map has been computed, (further) user input is received from the user in terms of a specification of one or more segments. Based on the segments, and optionally using the originally supplied user input, the collimator setting parameters are then computed, such as collimator lines. The collimator lines may be computed as edged of the specified segment. The edges may be computed to have a requisite clearance from the segment to provide a collimator setting at a requisite collimation tightness. The borders of the segments, thanks to the activation function, may be smooth. The further user input may include specification of as little as a single point on the smooth border. The complementing collimator lines may be thus computed as isolines for that border portion of the feature map value at that point. The value may thus specify the tightness parameter, as the values of the border portion decrease in generally in value as one progress across the border portion and away from the segment. Activation function values as encoded in the feature map may thus be harnessed herein as an indication for the desired collimator tightness. Values for the portion of segments may be used as previously described by constructing the isolines across the feature map to so find the desired segmentation. Alternatively, the collimator lines at a given tightness level are obtained by the user adjusting the threshold of the activation function for the hidden layer to produce different feature map versions with structures of different border transition smoothness. Segmentation of such structures thus result in edges that represent the sought after collimator lines at different tightness.

Thus, in embodiments the (further) input is merely a scalar value that is indicative of the desired collimator tightness, and this value is then used to compute from the feature map the complete collimator setting parameters. The user input may further comprise a designation of the respective segment.

At step S1230 the computed segmentation setting parameters are output and either displayed, possibly overlaid over the initial current input image, as received at step S1210, or the computed complemented collimator setting parameters are applied to the collimator blades actuators of the imaging apparatus to effect the desired collimation.

At step S1240, a check is made whether the current imaging geometry has been changed by the user. If it has changed, the collimator settings are abandoned, and the earlier steps S1220-S1230 are then repeated, but this time based on a new image that represents the new field of view as captured by the imaging apparatus in the new imaging geometry.

In the embodiments such as FIGS. 6-10, where the input comprises one or more images, this may be further enhanced by other contextual information of the imager system IA, such as c-arm position, fluoro flavor, procedure cards, identification of procedure phase, identification of a device in the image, protocol settings, system log file, etc. This contextual data may be processed alongside the image data. Processing may be in separate strand of layers, preferably fully connected to obtain feature maps in respect of the contextual data. Feature maps in respect of the contextual data may be concatenated with feature maps generated during processing of the image data, resulting in multi-channel feature maps.

In any one of the above described models in FIGS. 5, 6, and 8, input u may not only comprise a single (current) image $I_0$ as mentioned above, but a sequence of images. The sequence of images $I \in \{I_{t-n} \ldots I_{t-1}, I_0\}$ may be obtain in the same acquisition and represent imagery at different one or more previous time points. Including additional images from previous time points (such as for a given fluoroscopic run) could be beneficial to improve performance, especially in imaging procedures with frequent FOV changes. For example, in re-collimation where the FOV is enlarged or restricted for a given projection direction, certain image features may reappear or disappear. However, using previous images from previous time points for the same projection direction allows keeping some of the otherwise disappearing features, therefore boosting performance. For example, at the start of the imaging there is usually a large FOV (before collimation). Once collimation is applied, parts of the anatomy disappear, the FOV decreases. There are hence less features, and therefore the proposed method may become less accurate. Keeping previous one or more frames (before collimation) and co-pressing these for the current FOV will make performance and learning more stable and robust. In such embodiments with multiple image frame processing, a certain number of previous frames for a given run can be processed as a 3D image block including the current frame, with one dimension representing time. Multi-channel processing can be used as mentioned above for contextual data processing. In such embodiments with multiple image frame processing, recurrent layers may be used for more efficient processing of such time dependent data.

Figure 13:
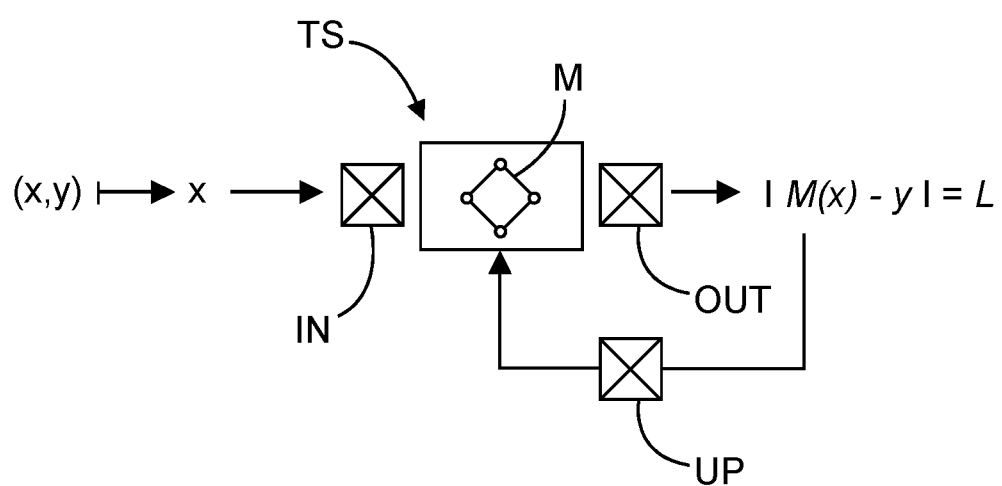
FIG. 13 shows a computer implemented training system for training a machine learning model for facilitating collimator adjustments.
Figure 14:
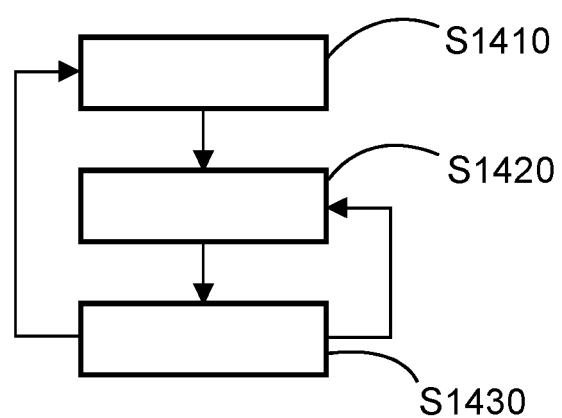
FIG. 14 is a flow chart of method of training a machine learning model for facilitating collimator adjustments.

Reference is now made to FIGS. 13 and 14 where training aspects are described in more detail.

Referring first to FIG. 13, this shows a training system TS for training the model M. Training operation includes learning model parameters, i.e. the weights of neural network as discussed in FIGS. 5-10, or of other neural network-type model, or indeed non-neural network type ML models.

The training data comprises k pairs of data $(x_k, y_k)$. k may run into the 10s, 100s or 1000s. The training data comprises for each pair k, training input data $x_k$ and an associated target $y_k$. The training data is thus organized in pairs k in particular for supervised learning schemes as for the model of FIG. 5 or FIG. 6. The model of FIG. 5 requires a data pair consisting of an image, and a set of line parameters $(a_i, b_i)$. One the other hand, model of FIG. 6 requires a data pair consisting of an image and "soft" collimation mask. Size of the collimation mask matches this of an input image. However, non-supervised learning schemes are also envisaged herein such as for the autoencoder type networks described above in FIGS. 8-10, where the training data is arranged in "trivial" pairs consisting of two identical images, e.g. $(x_k, x_k)$, where $x_k$ is an image.

For supervised learning, the training input data $x_k$ may be obtained from historical X-ray projection image data acquired for previous patient cases, and held in image repositories, such as the PACS of a HIS (hospital information system) for instance. The targets $y_k$ or "ground truth" may represent for examples label.

For example, training data set for the model M as per FIG. 5 or other supervised learning schemes, may be generated from a relatively large number of preferably (independent) different images $I_k$, (k=1 ... N>>30) acquired from different procedures and sampled from a relatively large patient population. The ground truth data may be generated by expert users. Each expert user looks at the training image and selects a desired collimator settings parameters. The training images may include partial collimator settings, obtainable by concealing the full collimation as represented in historic imagery. The expert user hence guesses during labelling the missing collimation parameters using their expert knowledge. The labeling exercise may thus be organized and administered as a "game". The collimator setting parameters may represent collimator blade position, and may be represented by a parametric equation with coefficients a, b for the collimator lines as described above. The lines may be lineal or curved. A patch of pixels of an arbitrary size may be extracted around the respective line, paired with parameters (a·b), and may be stored in memory as 2-tuples in association with training input images.

In the described encoder-decoder scheme in FIG. 6, collimation masks are created from the collimator settings parameters provided by the expert users. For instance by generating a largest possible area that is encapsulated by intersecting collimation lines.

In the described autoencoder schemes in FIG. 8, no labels are required and ground truth equals the training inputs $y_k = x_k$.

If the training is to include contextual data, there is in general no contextual data included in the target $y_k$ for any pair k, such as in the multi-strand models as discussed above in relation to FIG. 6. In other words, for learning with contextual data the pairs may in general have a form $((x_k, c), y_k)$, with non-image context data c only associated with the training input $x_k$, but not with the target $y_k$.

In the training phase, an architecture of a machine learning model M, such as the shown CNN networks in FIGS. 5-10 are pre-populated with initial set of weights. Random initialization or pre-training on a synthetic or independent by identically distributed training data or combination may be used to pre-populate the weights. The weights θ of the model NN represent a parameterization $M^\theta$, and it is the object of the training system TS to optimize and hence adapt the parameters θ based on the training data $(x_k, y_k)$ pairs. In other words, the learning can be formulized mathematically as an optimization scheme where a cost function F is minimized although the dual formulation of maximizing a utility function may be used instead.

Assuming for now the paradigm of a cost function F, this measures the aggregated residue(s), that is, the error incurred between data estimated by the neural network model NN and the targets as per some or all of the training data pairs k:

$$\operatorname{argmin}_\theta L = \sum_k \left\| M^\theta(x_k), y_k \right\| \quad (1)$$

In eq. (1) and below, function MO denotes the result of the model M applied to input x.

Specifically, the network M in FIG. 5 is pre-trained on the task to regress the input data into parameters for the missing collimator lines. Thus, the regression may be into one or more coefficients "a" (x-intercept) and "b" (y-intercept) that define the collimator lines in a parametric way. Network FIG. 5 may be trained using an MSE loss function F that compares predicted lines with the associated target lines, possibly selected by expert users in a labelling task. Other cost functions may be used.

In the feature map based processing of FIGS. 6-10, the model M is preferably an autoencoder, where the task is to regress the input image into itself. If non-autoencoder networks are used for feature map based processing, any network M may be used, and this can be trained on an arbitrary task classification or regression, using training imagery than represents scenarios most likely to be encountered during the deployment. For instance, one could train the network M to image detect objects on the x-ray images, such as TEE probe, guidewires. The task here is irrelevant is in this embodiment it will be only the internal feature maps from a hidden layer at a suitable depth that will be used. In the autoencoder, the preferred feature map is the code, the feature map generated at the last convolutional layer of the encoder EC portion. More specifically, the autoencoder type network of FIGS. 6-10 is preferably trained using unsupervised feature learning paradigm. It is assumed that the encoder subnetwork EC will learn the most relevant features that reduced to a low-dimensional latent representation, the code χ, that can still be decoded by the decoder DC to match the input image. The consistency between input and output may be optimized using as loss function F any one of mean squared error (MSE), mean absolute error (MAE), structural similarity (SSIM), binary cross-entropy, adversarial loss or any combination of the foregoing.

In training, the training input data $x_k$ of a training pair is propagated through the initialized network M. Specifically, the training input $x_k$ for a k-th pair is received at an input IL, passed through the model and is then output at output OL as output training data $M^\theta(x)$. A suitable measure $\|\cdot\|$ as implemented by any of the cost functions F mentioned above (such as a p-norm, squared differences, or other) measures the difference, also referred to herein as residue, between the actual training output $M^\theta(x_k)$ produced by the model M, and the desired target $y_k$.

The output training data $M(x_k)$ is an estimate for target $y_k$ associated with the applied input training image data $x_k$. In general, there is an error between this output $M(x_k)$ and the associated target $y_k$ of the presently considered k-th pair. An optimization scheme such as backward/forward propagation or other gradient based methods may then be used to adapt the parameters θ of the model M so as to decrease the residue for the considered pair $(x_k, y_k)$ or a subset of training pairs from the full training data set.

After one or more iterations in a first, inner, loop in which the parameters θ of the model are updated by updater UP for the current pair $(x_k, y_k)$, the training system TS enters a second, an outer, loop where a next training data pair $x^{k+1}$, $y^{k+1}$ is processed accordingly. The structure of updater UP depends on the optimization scheme used. For example, the inner loop as administered by updater UP may be implemented by one or more forward and backward passes in a forward/backpropagation algorithm. While adapting the parameters, the aggregated, for example summed, residues of all the training pairs are considered up to the current pair, to improve the objective function. The aggregated residue can be formed by configuring the objective function F as a sum of squared residues such as in eq. (1) of some or all considered residues for each pair. Other algebraic combinations instead of sums of squares are also envisaged.

Optionally, one or more batch normalization operators ("BN", not shown) may be used. The batch normalization operators may be integrated into the model M, for example coupled to one or more of the convolutional operator in a layer. BN operators allow mitigating vanishing gradient effects, the gradual reduction of gradient magnitude in the repeated forward and backward passes experienced during gradient-based learning algorithms in the learning phase of the model M The batch normalization operators BN may be used in training, but may also be used in deployment.

The training system as shown in FIG. 13 can be considered for all learning schemes, in particular supervised schemes. Unsupervised learning schemes may also be envisaged herein in alternative embodiments. GPUs or TPUs may be used to implement the training system TS.

The fully trained machine learning module M may be stored in one or more memories or databases, and can be made available as pre-trained machine learning models for use in the user assistance system USYS as proposed herein. The trained model M may be made available in a cloud service. Access can either be offered free of charge or their use can be granted via license-pay or pay-per-use scheme.

Referring now to FIG. 14, this shows a flow chart of a method of training a machine learning model in any of the embodiments discussed above.

A suitable training data set is procured as described above at FIG. 13. Preferably, supervised learning schemes are envisaged herein although this is not a necessity as unsupervised learning setups are also envisaged herein.

In supervised learning, the training data includes suitable pairs of data items, each pair including training input data and associated therewith a target training output data. Specifically, the pairs comprise. The imagery may be procured from historic patient records such as a PACS or other data repository, as described above.

With continued reference to FIG. 14, at step S1410 training data is received in the form of pairs $(x_k, y_k)$. Each pair includes the training input $x_k$ and the associated target $y_k$. $x_k$, as defined in FIG. 13 above.

At step S1420, the training input $x_k$ is applied to an initialized machine learning model NN to produce a training output.

A deviation, or residue, of the training output $M(x_k)$ from the associated target $y_k$ is quantified by a cost function L. One or more parameters of the model are adapted at step S1430 in one or more iterations in an inner loop to improve the cost function. For instance, the model parameters are adapted to decrease residues as measured by the cost function. The parameters include in particular weights of an artificial neural network M.

The training method then returns in an outer loop to step S1410 where the next pair of training data is fed in. In step S1420, the parameters of the model are adapted so that the aggregated residues of all pairs considered are decreased, in particular minimized. The cost function quantifies the aggregated residues. Forward-backward propagation or similar gradient-based techniques may be used in the inner loop.

More generally, the parameters of the model NN are adjusted to improve objective function F which is either a cost function or a utility function. In embodiments, the cost function is configured to the measure the aggregated residues. In embodiments the aggregation of residues is implemented by summation over all or some residues for all pairs considered. If unsupervised learning is used, especially in the autoencoder type NN network embodiments, there are no, or only "nominal" pairs where $x_k = y_k$.

The method may be implemented on one or more general-purpose processing units TS, preferably having processors capable for parallel processing to speed up the training. The components of the training system TS may be implemented as one or more software modules, run on one or more general-purpose processing units PU such as a workstation associated with the imager IA, or on a server computer associated with a group of imagers.

Whilst the system USYS and related methods have been described with main reference to X-ray imaging, this is not at the exclusion of other applications, such as collimator adjustments for radiation therapy delivery, such as multi-leaf collimators or linear accelerator devices, other. Collimation for external-beam radiation therapies, or proton therapies (such as in ophthalmological treatments or other) are also envisaged herein.

The components of the image system USYS may be implemented as one or more software modules, run on one or more general-purpose processing units PU such as a workstation associated with the imager XI, or on a server computer associated with a group of imagers.

Alternatively, some or all components of the image processing system IPS may be arranged in hardware such as a suitably programmed microcontroller or microprocessor, such an FPGA (field-programmable-gate-array) or as a hard-wired IC chip, an application specific integrated circuitry (ASIC), integrated into the imaging system XI. In a further embodiment still, the image processing system IPS may be implemented in both, partly in software and partly in hardware.

The different components of the image processing system IPS may be implemented on a single data processing unit PU. Alternatively, some or more components are implemented on different processing units PU, possibly remotely arranged in a distributed architecture and connectable in a suitable communication network such as in a cloud setting or client-server setup, as a web-hosted service etc. This allows serving multiple geographically distributed imaging sites, either across a single medical facility or across multiple medical facilities.

One or more features described herein can be configured or implemented as or with circuitry encoded within a computer-readable medium, and/or combinations thereof.

Circuitry may include discrete and/or integrated circuitry, a system-on-a-chip (SOC), and combinations thereof, a machine, a computer system, a processor and memory, a computer program.

In another exemplary embodiment of the present invention, a computer program or a computer program element is provided that is characterized by being adapted to execute the method steps of the method according to one of the preceding embodiments, on an appropriate system.

The computer program element might therefore be stored on a computer unit, which might also be part of an embodiment of the present invention. This computing unit may be adapted to perform or induce a performing of the steps of the method described above. Moreover, it may be adapted to operate the components of the above-described apparatus. The computing unit can be adapted to operate automatically and/or to execute the orders of a user. A computer program may be loaded into a working memory of a data processor. The data processor may thus be equipped to carry out the method of the invention.

This exemplary embodiment of the invention covers both, a computer program that right from the beginning uses the invention and a computer program that by means of an up-date turns an existing program into a program that uses the invention.

Further on, the computer program element might be able to provide all necessary steps to fulfill the procedure of an exemplary embodiment of the method as described above.

According to a further exemplary embodiment of the present invention, a computer readable medium, such as a CD-ROM, is presented wherein the computer readable medium has a computer program element stored on it which computer program element is described by the preceding section.

A computer program may be stored and/or distributed on a suitable medium (in particular, but not necessarily, a non-transitory medium), such as an optical storage medium or a solid-state medium supplied together with or as part of other hardware, but may also be distributed in other forms, such as via the internet or other wired or wireless telecommunication systems.

However, the computer program may also be presented over a network like the World Wide Web and can be downloaded into the working memory of a data processor from such a network. According to a further exemplary embodiment of the present invention, a medium for making a computer program element available for downloading is provided, which computer program element is arranged to perform a method according to one of the previously described embodiments of the invention.

It has to be noted that embodiments of the invention are described with reference to different subject matters. In particular, some embodiments are described with reference to method type claims whereas other embodiments are described with reference to the device type claims. However, a person skilled in the art will gather from the above and the following description that, unless otherwise notified, in addition to any combination of features belonging to one type of subject matter also any combination between features relating to different subject matters is considered to be disclosed with this application. However, all features can be combined providing synergetic effects that are more than the simple summation of the features.

While the invention has been illustrated and described in detail in the drawings and foregoing description, such illustration and description are to be considered illustrative or exemplary and not restrictive. The invention is not limited to the disclosed embodiments. Other variations to the disclosed embodiments can be understood and effected by those skilled in the art in practicing a claimed invention, from a study of the drawings, the disclosure, and the dependent claims.

In the claims, the word "comprising" does not exclude other elements or steps, and the indefinite article "a" or "an" does not exclude a plurality. A single processor or other unit may fulfill the functions of several items re-cited in the claims. The mere fact that certain measures are re-cited in mutually different dependent claims does not indicate that a combination of these measures cannot be used to advantage. Any reference signs in the claims should not be construed as limiting the scope.

The invention claimed is:

1. A system for determining a collimator adjustment, the system comprising:
   a processor configured to:
   receive input data including user input data including a first collimator setting for a collimator of an X-ray imaging apparatus; and
   compute a second collimator setting for the collimator based the input data.

2. The system of claim 1, wherein the processor is further configured to compute the second collimator setting by applying a trained machine learning model, or to compute the second collimator setting based on output data provided by a trained machine learning model.

3. The system of claim 2, wherein the output data provided by the trained machine learning model includes a feature map or heat map derived from a feature map.

4. The system of claim 2, wherein the trained machine learning model is an artificial neural network.

5. The system of claim 2, wherein the processor is further configured to segment the feature or heat map into at least one segment and compute the second collimator setting based on the at least one segment.

6. The system of claim 1, wherein the input data further includes at least one input image acquired by the X-ray imaging apparatus.

7. The system of claim 1, wherein the first collimator setting includes a specification of a geometrical point, curve, or line in i) the, or a, an input image acquired by the X-ray imaging apparatus or ii) in a feature map or heat map.

8. The system of claim 1, further comprising a user input device for capturing the user input data, the user input device including one or more of: a graphical user interface, an eye tracking device, a gesture detection device, and a voice processor.

9. The system of claim 1, wherein the X-ray imaging apparatus is configured to assume different imaging geometries, and the processor is further configured to adjust the second collimator setting in response to the X-ray imaging apparatus changing to a different imaging geometry.

10. The system of claim 1, wherein the second collimator setting parameter specifies a collimation tightness.

11. The system of claim 2, further comprising a second processor configured to perform training of the machine learning model.

12. The system of claim 11, wherein the second processor is configured to performed unsupervised training of the machine learning model.

13. A method for facilitating collimator adjustment in X-ray imaging or radiation therapy delivery, the method comprising:
   receiving input data including a first collimator setting for a collimator of an X-ray imaging apparatus; and computing a second collimator setting for the collimator based the input data.

14. A non-transitory computer-readable storage medium having stored a computer program comprising instructions, which, when being executed by a processor, cause the processor to:
 receive input data including user input data including a first collimator setting for a collimator of an X-ray imaging apparatus; and
 compute a second collimator setting for the collimator based the input data.

* * * * *